United States Patent
Dilmanian et al.

(10) Patent No.: US 11,628,312 B2
(45) Date of Patent: *Apr. 18, 2023

(54) SYSTEM AND METHOD FOR DUAL-USE COMPUTED TOMOGRAPHY FOR IMAGING AND RADIATION THERAPY

(71) Applicant: THE RESEARCH FOUNDATION FOR STATE UNIVERSITY OF NY, Albany, NY (US)

(72) Inventors: F. Avraham Dilmanian, Great Neck, NY (US); Mark Schweitzer, Dix Hills, NY (US); Jameson Baker, East Northport, NY (US); Renee Cattell, Selden, NY (US)

(73) Assignee: THE RESEARCH FOUNDATION FOR THE STATE UNIVERSITY OF NEW YORK, Albany, NY (US)

( * ) Notice: Subject to any disclaimer, the term of this patent is extended or adjusted under 35 U.S.C. 154(b) by 259 days.

This patent is subject to a terminal disclaimer.

(21) Appl. No.: 16/760,819

(22) PCT Filed: Nov. 6, 2018

(86) PCT No.: PCT/US2018/059401
§ 371 (c)(1),
(2) Date: Apr. 30, 2020

(87) PCT Pub. No.: WO2019/090314
PCT Pub. Date: May 9, 2019

(65) Prior Publication Data
US 2020/0289851 A1    Sep. 17, 2020

Related U.S. Application Data

(60) Provisional application No. 62/581,952, filed on Nov. 6, 2017.

(51) Int. Cl.
*A61N 5/10* (2006.01)
*A61B 6/03* (2006.01)
(Continued)

(52) U.S. Cl.
CPC ............. *A61N 5/1049* (2013.01); *A61B 6/03* (2013.01); *A61B 6/032* (2013.01); *A61B 6/035* (2013.01);
(Continued)

(58) Field of Classification Search
CPC ..... A61B 6/032; A61B 6/0407; A61B 6/0492; A61B 6/06; A61B 6/42; A61B 6/4291;
(Continued)

(56) References Cited

U.S. PATENT DOCUMENTS

| 5,008,907 A | 4/1991 | Norman et al. |
| 5,054,041 A | 10/1991 | Hampel |

(Continued)

FOREIGN PATENT DOCUMENTS

| EP | 0290165 A1 | 11/1988 |
| JP | 2622064 B2 | 6/1997 |

(Continued)

OTHER PUBLICATIONS

Int'l Search Report and Written Opinion PCT/US2018/059401, dated Jan. 23, 2019.

(Continued)

*Primary Examiner* — Mark R Gaworecki
(74) *Attorney, Agent, or Firm* — Betsy Kingsbury Dowd; BKDowd Law, P.C.

(57) ABSTRACT

A system and method for delivering microbeam radiation therapy (MRT) includes a computed tomography scanner ("CT") configured to generate tomographic images of a subject, or patient, the scanner including an imaging apparatus, a gantry with an opening for positioning the patient (Continued)

therein, an axis of rotation around which the gantry rotates, and an x-ray source mounted to and rotatable with the gantry. The system includes a bed for patient positioning within the gantry opening and a multi-slit collimator removably mounted downstream of the x-ray source for delivering an array of microbeams of MRT to a targeted portion of the patient. Switching between MRT and CT is provided, and MRT modes of operation include a stationary mode, and continuous and step-wise rotational modes.

17 Claims, 10 Drawing Sheets

(51) Int. Cl.
    *A61B 6/04*     (2006.01)
    *A61B 6/06*     (2006.01)
    *A61B 6/00*     (2006.01)

(52) U.S. Cl.
    CPC .............. *A61B 6/0407* (2013.01); *A61B 6/06* (2013.01); *A61N 5/1042* (2013.01); *A61N 5/1067* (2013.01); *A61N 5/1081* (2013.01); *A61B 6/04* (2013.01); *A61B 6/0442* (2013.01); *A61B 6/501* (2013.01); *A61B 6/508* (2013.01); *A61N 2005/1054* (2013.01); *A61N 2005/1061* (2013.01); *A61N 2005/1074* (2013.01); *A61N 2005/1095* (2013.01)

(58) Field of Classification Search
    CPC ....... A61B 6/44; A61B 6/4411; A61B 6/4429; A61B 6/447; A61B 6/505; A61B 6/52; A61B 6/5294; A61B 6/54; A61B 6/542; A61B 6/589; A61B 34/10; A61B 34/20; A61B 2034/107; A61B 2034/2065; A61B 2560/04; A61B 2560/0443; A61B 2562/18; A61B 6/03; A61B 6/035; A61B 6/04; A61B 6/0442; A61B 6/501; A61B 6/508; A61N 5/10; A61N 5/103; A61N 5/1042; A61N 5/1045; A61N 5/1048; A61N 5/1049; A61N 5/1065; A61N 5/1067; A61N 5/1069; A61N 5/107; A61N 5/1077; A61N 2005/1019; A61N 2005/1054; A61N 2005/1061; A61N 2005/1081; A61N 2005/1095; A61N 5/1081; A61N 2005/1074; G01N 2223/30; G01N 2223/308; G01N 2223/314; G01N 2223/316; G01N 2223/32; G01N 2223/321; G21K 1/02; G21K 1/025; G21K 1/04; G21K 1/043; G21K 1/046; G21K 5/00; G21K 5/04; G21K 5/10; H01L 27/144; H01L 27/146; H01L 27/14601; H01L 27/14618; H01L 27/14625; H01J 37/09; H01J 37/147; H01J 37/1472; H01J 37/16; H01J 37/20; H01J 37/244; H01J 37/30; H01J 37/3002; H01J 37/302; H01J 2237/04; H01J 2237/045; H01J 2237/0451; H01J 2237/0453; H01J 2237/0455; H01J 2237/0456; H01J 2237/06; H01J 2237/061; H01J 2237/083; H01J 2237/0835

See application file for complete search history.

(56) References Cited

U.S. PATENT DOCUMENTS

| | | | |
|---|---|---|---|
| 5,090,037 A | 2/1992 | Toth et al. | |
| 5,966,422 A | 10/1999 | Dafni et al. | |
| 6,118,839 A | 9/2000 | Dafni et al. | |
| 6,185,271 B1 | 2/2001 | Kinsinger et al. | |
| 6,229,870 B1 | 5/2001 | Morgan | |
| 6,246,742 B1 | 6/2001 | Besson et al. | |
| 6,385,278 B1 | 5/2002 | Hsieh | |
| 6,449,340 B1 | 9/2002 | Tybinkowski et al. | |
| 6,670,614 B1 | 12/2003 | Plut et al. | |
| 6,714,627 B1* | 3/2004 | Brown | G21K 1/04 378/65 |
| 6,940,948 B1 | 9/2005 | Treriakov | |
| 7,283,610 B2* | 10/2007 | Low | A61N 5/1027 378/65 |
| 7,324,623 B2 | 1/2008 | Heuscher | |
| 7,458,118 B2 | 12/2008 | Bak | |
| 7,564,945 B2 | 7/2009 | Kim | |
| 7,696,499 B2 | 4/2010 | Miller | |
| 7,746,979 B2* | 6/2010 | Dilmanian | A61N 5/1084 378/65 |
| 8,536,547 B2 | 9/2013 | Maurer, Jr. et al. | |
| 8,915,833 B1* | 12/2014 | Sahadevan | A61N 5/1084 600/1 |
| 9,042,514 B2 | 5/2015 | Abraham et al. | |
| 9,687,200 B2 | 6/2017 | Maurer, Jr. | |
| 9,763,631 B2 | 9/2017 | Hefetz et al. | |
| 10,315,050 B2 | 6/2019 | Maurer et al. | |
| 10,335,611 B2 | 7/2019 | Maurer, Jr. et al. | |
| 10,702,711 B2* | 7/2020 | Kundapur | G21K 1/025 |
| 10,814,146 B2* | 10/2020 | Dilmanian | A61B 6/06 |
| 11,045,151 B2 | 6/2021 | Jensen et al. | |
| 11,259,762 B2 | 3/2022 | Zhang | |
| 2001/0048732 A1 | 12/2001 | Wilson et al. | |
| 2003/0007601 A1 | 1/2003 | Jaffrey et al. | |
| 2005/0100126 A1 | 5/2005 | Mistretta et al. | |
| 2005/0135560 A1 | 6/2005 | Dafni et al. | |
| 2006/0072699 A1* | 4/2006 | Mackie | A61B 6/032 378/4 |
| 2006/0159220 A1 | 7/2006 | Heuscher et al. | |
| 2006/0176997 A1* | 8/2006 | Dilmanian | A61N 5/1042 378/65 |
| 2006/0177002 A1 | 8/2006 | Toth et al. | |
| 2006/0193430 A1 | 8/2006 | Kuhn | |
| 2007/0238957 A1 | 10/2007 | Yared | |
| 2007/0280408 A1 | 12/2007 | Zhang | |
| 2008/0063142 A1 | 3/2008 | Weil | |
| 2008/0123803 A1 | 5/2008 | De Man et al. | |
| 2008/0192892 A1* | 8/2008 | Dilmanian | A61N 5/1045 378/65 |
| 2009/0074134 A1 | 3/2009 | Jeffery et al. | |
| 2009/0093863 A1 | 4/2009 | Dilmanian | |
| 2009/0025755 A1 | 10/2009 | Dafni et al. | |
| 2010/0074400 A1 | 3/2010 | Sendai | |
| 2010/0187446 A1* | 7/2010 | Dilmanian | A61N 5/1042 250/492.3 |
| 2010/0246752 A1 | 9/2010 | Heuscher et al. | |
| 2010/0260317 A1* | 10/2010 | Chang | A61N 5/103 378/65 |
| 2010/0274120 A1 | 10/2010 | Heuscher et al. | |
| 2011/0218429 A1 | 9/2011 | Harada | |
| 2011/0228999 A1 | 9/2011 | Hsieh | |
| 2012/0106695 A1 | 5/2012 | Fan et al. | |
| 2012/0189094 A1 | 7/2012 | Neushul et al. | |
| 2012/0257709 A1 | 10/2012 | Oota et al. | |
| 2013/0308746 A1 | 11/2013 | Ueki | |
| 2013/0308749 A1 | 11/2013 | Zilberstein et al. | |
| 2014/0247919 A1 | 9/2014 | Zhang et al. | |
| 2014/0369462 A1 | 12/2014 | Lacey | |
| 2015/0173692 A1 | 6/2015 | Heuscher | |
| 2016/0081635 A1 | 3/2016 | Divine et al. | |
| 2016/0081641 A1 | 3/2016 | Bouhnik et al. | |

(56) References Cited

U.S. PATENT DOCUMENTS

2016/0278719 A1 9/2016 Jensen et al.
2017/0036043 A1 2/2017 Dilmanian et al.
2019/0126070 A1 5/2019 Hsieh

FOREIGN PATENT DOCUMENTS

| JP | H1071141 A | 3/1998 | |
|---|---|---|---|
| JP | 2774790 B2 | 7/1998 | |
| JP | 4936687 B2 | 5/2012 | |
| WO | WO-2007014090 A2 * | 2/2007 | ........... A61B 5/0555 |
| WO | 2016126829 A1 | 8/2016 | |

OTHER PUBLICATIONS

Slatkin DN, Spanne P, Dillmanian FA, Gebbers JO, Laissue JA. Subacute neuropathological effects of microplanar beams of x-rays from a synchrotron wiggler. Proc Natl Acad Sci U S A. 1995;92(19):8783-7.

Dilmanian FA, Qu Y, Liu S, Cool CD, Gilbert J, Hainfeld JF, Kruse CA, Laterra J, Lenihan D, Nawrocky MM, Pappas G, Sze CI, Yuasa T, Zhong N, Zhong Z, McDonald JW. X-ray microbeams: Tumor therapy and central nervous system research. Nucl Instrum Methods Phys Res A. 2005;548(1-2):30-37.

Serduc R, Verant P, Vial JC, Farion R, Rocas L, Remy C, Fadlallah T, Brauer E, Bravin A, Laissue J, B:Atmann H, Van Der Sanden B. In vivo two-photon microscopy study of short-term effects of microbeam irradiation on normal mouse brain microvasculature. Int J Radiat Oncol Biol Phys. 2006;64(5):1519-27.

Dilmanian FA, Zhong Z, Bacarian T, Beneviste H, Romanelli P, Wang R, Welwart J, Yuasa T, Rosen EM, Anschel DJ. Interlaced x-ray microplanar beams: a radiosurgery approach with clinical potential. Proc Natl Acad Sci U S A. 2006;103(25):9709-14.

Laissue JA, Blatmann H, Wagner HP, Grotzer MA, Slatkin DN. Prospects for microbeam radiation therapy of brain tumours in children to reduce neurological sequelae. Dev Med Child Neurol. 2007;49(8):577-81.

Dilmanian FA, Qu Y, Feinendegen LE, Pena LA, Bacarian T, Henn FA, Kalef_Ezra J, Liu S, Zhong Z, McDonald JW. Tissue-sparing effect of x-ray microplanar beams particularly in the CNS: is a bystander effect involved? Exp Hematol. Apr. 2007;35(4 Suppl 1):69-77.

Dilmanian FA, Jenkins AL, Olschowka J, Zhong Z, Park JY, Desnoyers NR, Sobotka S, Fois GR, Messina CR, Morales M, Hurley SD, Trojanczyk LA, Ahmad S, Sharabi N, Coyle PK, Meek AG, and O'Banion MK. X-ray microbeam irradiation of the contusion-injured rat spinal cord temporarily improves hind-limb function. Radiat. Res. 179:76-88, 2013.

Yuan H, Zhang L, Frank JE, Iinscoe CR, Burk LM, Hadsell M, Lee YZ, Lu J,4, Chang S, Zhou O. Treating Brain Tumor with Microbeam Radiation Generated by a Compact Carbon-Nanotube-Based Irradiator: Initial Radiation Efficacy Study. Radiat Res. Sep. 2015;184(3):322-33. doi: 10.1667/RR13919.1. Epub Aug. 25, 2015.

Marples B, McGee M, Callan S, Bowen SE, Thibodeau BJ, Michael DB, Wilson GD, Maddens ME, Fontanesi J, Martinez AA. Cranial irradiation significantly reduces beta amyloid plaques in the brain and improves cognition in a murine model of Alzheimer's Disease (AD). Radiother Oncol. Jan. 2016;118(1):43-51. doi 10.1016/j.radonc.2015.10.019. Epub Nov. 23, 2015.

Calvo W, Hopewell J W, Reinhold H S, Yeung T K. Time- and dose-related changes in the white matter of the rat brain after single doses of X rays. Brit. J. Radiol. 1998; 61: 1043-1052.

* cited by examiner

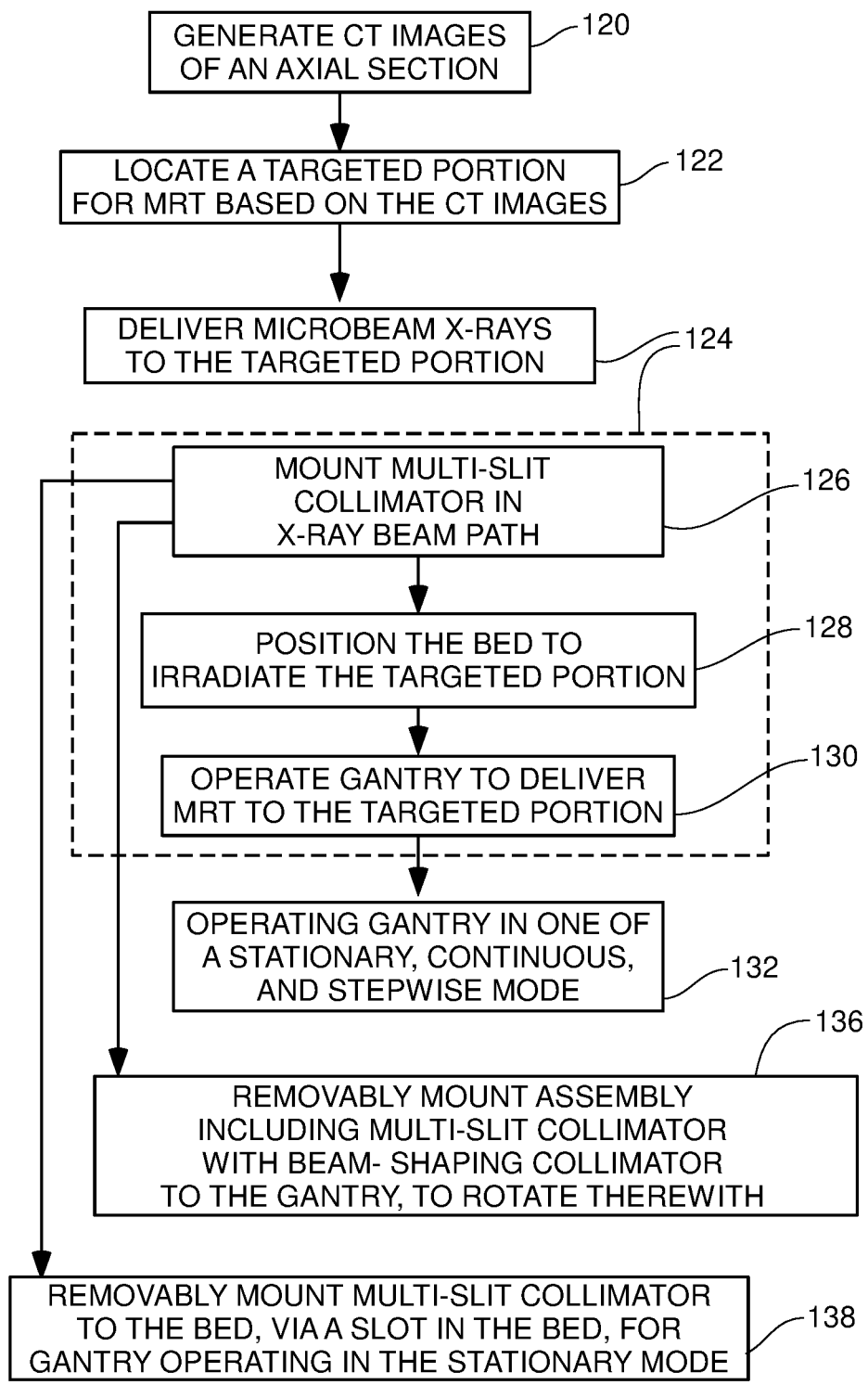

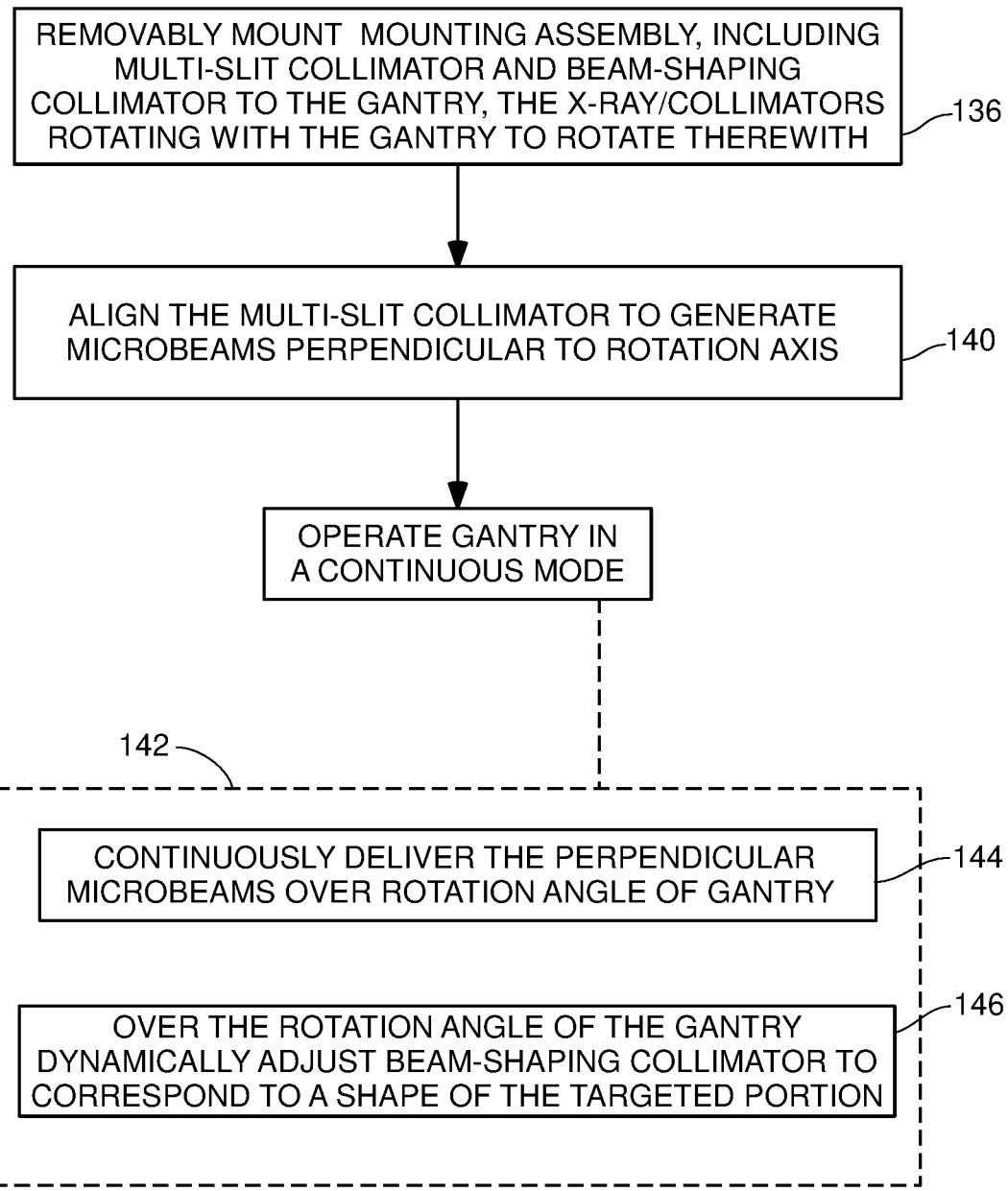

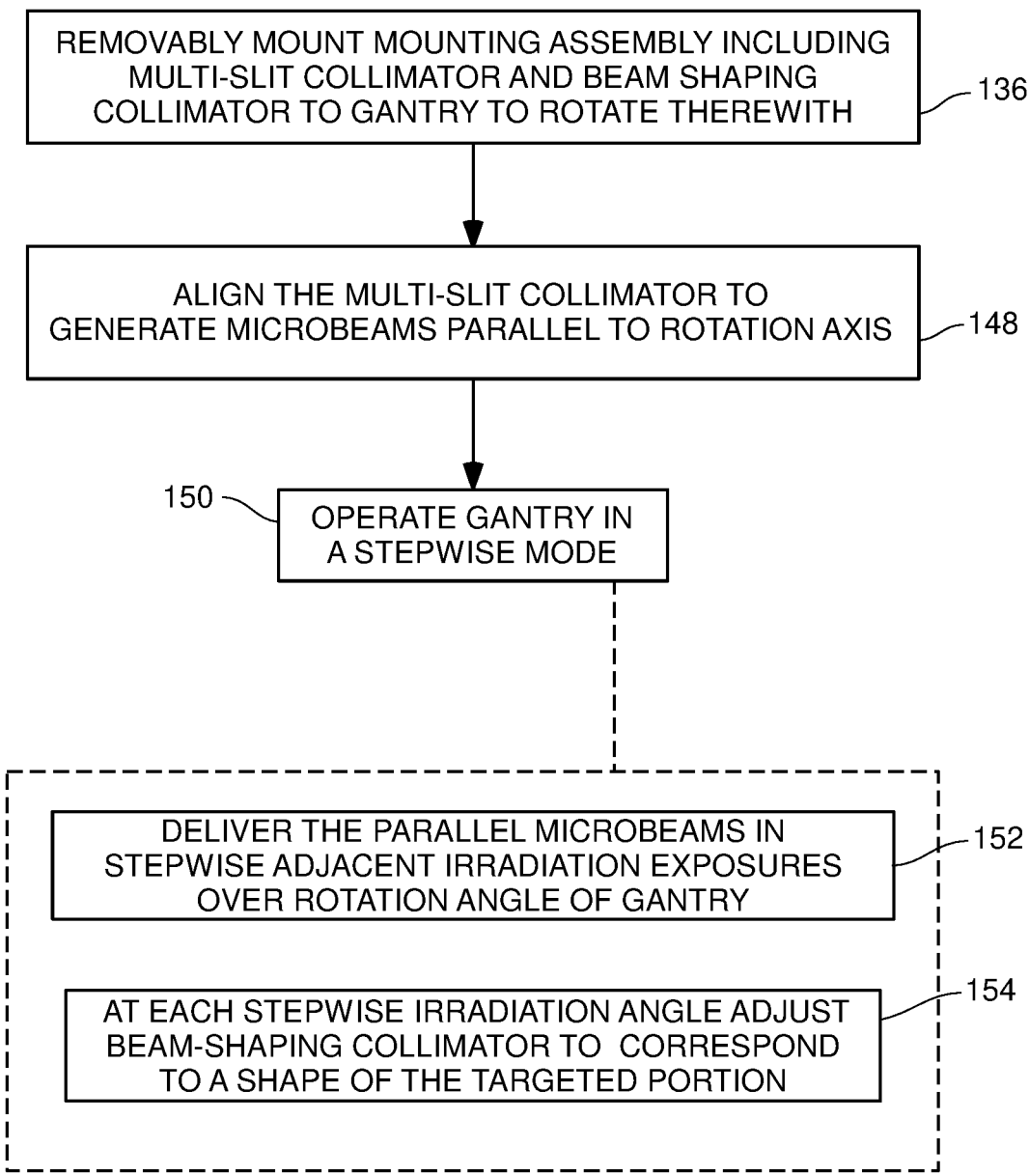

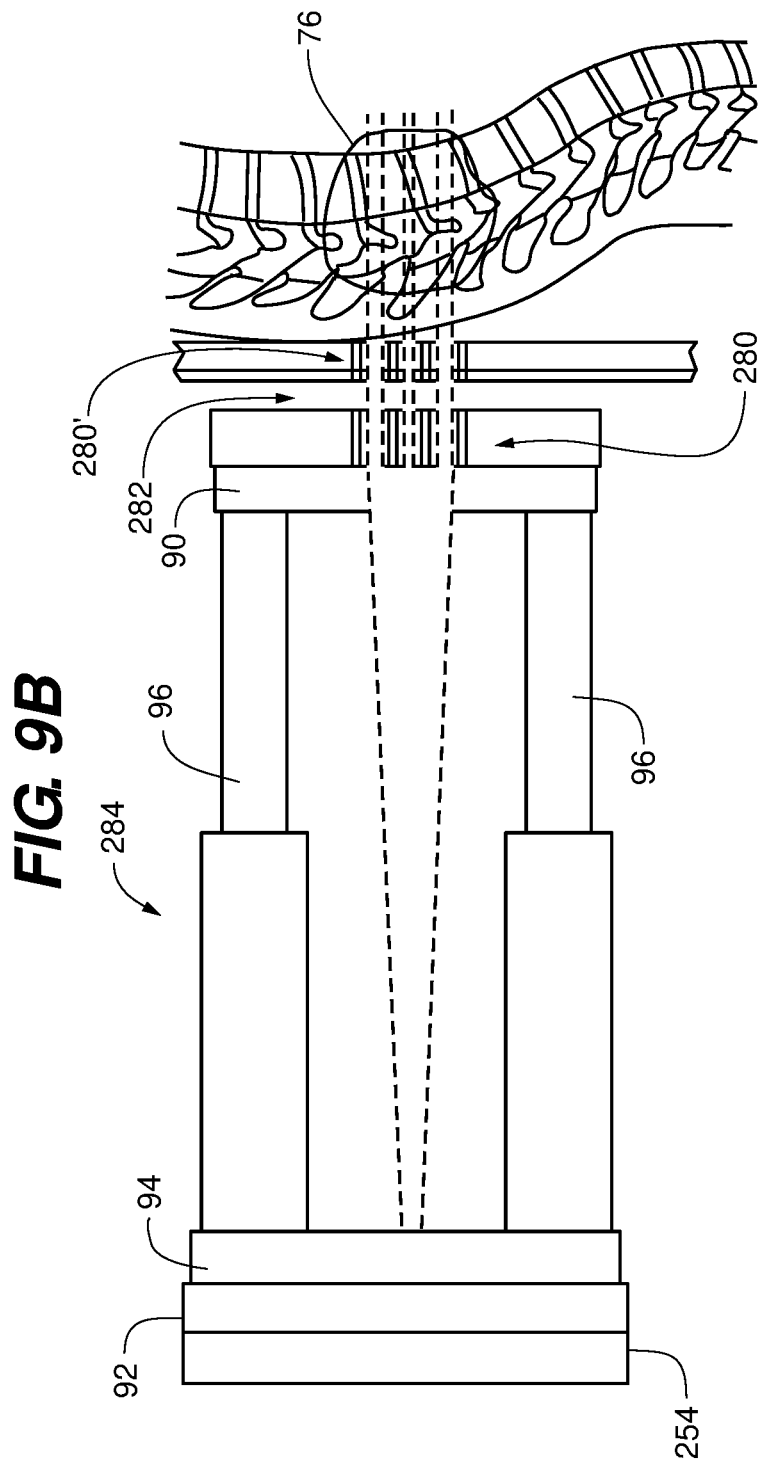

SYSTEM AND METHOD FOR DUAL-USE COMPUTED TOMOGRAPHY FOR IMAGING AND RADIATION THERAPY

CROSS-REFERENCE TO RELATED APPLICATIONS

This application is a U.S. national phase filing of Int'l Application Ser. No. PCT/US2018/059401, with an international filing date of Nov. 6, 2018, which claims the benefit of and priority to U.S. Provisional Application Ser. No. 62/581,952 entitled "SYSTEM AND METHOD FOR DUAL-USE COMPUTED TOMOGRAPHY FOR IMAGING AND RADIATION THERAPY," filed Nov. 6, 2017, the entirety of each of which is hereby incorporated herein by reference thereto.

FIELD OF DISCLOSURE

The present disclosure relates generally to x-ray radiation therapy and particularly to x-ray radiation therapy using segmented beams of radiation.

BACKGROUND

Conventionally, therapeutic high-energy x-ray radiation is delivered to patients after diagnostic imaging has identified a target region for treatment. For example, computed tomography, or "CT" scanners may be used to locate a targeted region for radiation treatment. At a later time, the radiation treatment is performed using a different device configured to deliver the therapeutic x-ray radiation to the patient. Earlier acquired x-ray images, axial sections of CT images, or other data acquired through 3-D rendering of the reconstructed CT images are used to direct the therapeutic x-ray radiation as accurately as possible at the targeted region.

The accuracy in matching the x-ray irradiated region to the targeted region identified from the CT scanner data is critical, since errors in positioning the patient in the radiation treatment device cause unnecessary exposure of healthy tissue to the high-energy x-ray radiation.

Accordingly, there is a need for a method and system for performing x-ray radiotherapy that minimizes damage of healthy tissue that otherwise occurs when using conventional x-ray radiation therapy and modalities.

SUMMARY

Features of the disclosure will become apparent from the following detailed description considered in conjunction with the accompanying drawings. It is to be understood, however, that the drawings are designed as an illustration only and not as a definition of the limits of this disclosure.

The present disclosure is directed to a method and system for utilizing an x-ray tube mounted on a computed tomography ("CT") scanner to clinically administer x-ray microbeams to patients. The present method and system for performing microbeam radiotherapy therapy ("MRT") using an x-ray source of a CT scanner may minimize damage of healthy tissue proximal to a targeted portion, and also may minimize damage of healthy tissue that can otherwise occur in conventional systems that require repositioning of a patient for radiation therapy, after a computed tomography imaging scan.

The present disclosure is also directed to a system for delivering microbeam x-ray radiation therapy to a subject, the system including a computed tomography ("CT") scanner. The CT scanner includes imaging apparatus, a gantry having an inner surface surrounding an opening for positioning a subject therein, an axis of rotation around which the gantry rotates, and an x-ray source mounted to and rotatable with the gantry. The CT scanner is configured to generate tomographic images of an axial section of a subject positioned within the opening.

The system also includes a bed on which the subject is positioned within the opening; and a multi-slit collimator removably mounted downstream of the x-ray source for delivering an array of microbeams of therapeutic x-ray radiation to a targeted portion of the axial section.

In one aspect, the system further includes positioning elements operatively connected to the multi-slit collimator and removably mounted with the multi-slit collimator to the gantry for positioning the multi-slit collimator downstream of, and rotationally moving with, the x-ray source on the gantry.

The positioning elements, in aspects, are fixed in length, the multi-slit collimator being positioned at a fixed distance from the x-ray source.

In other aspects, the positioning elements include spring-loaded junctions, a distance between the multi-slit collimator and the x-ray source being springedly shortened upon contact of a distal end of the positioning elements with the bed.

In additional aspects, the system may further include a beam-shaping collimator positioned upstream of the multi-slit collimator, which is removably mounted along with the multi-slit collimator and the positioning elements to the gantry.

The beam-shaping collimator may be a multi-leaf collimator.

In another aspect, the system further includes a control module configured to switchably operate the gantry in a CT scanner mode, and in a microbeam radiation therapy ("MRT") mode to deliver microbeam radiation to the subject with the multi-slit collimator positioned downstream of the x-ray source.

The system may further include a shutter formed of an x-ray absorbing material, which is operable to automatically cover the detectors of the CT scanner in the MRT mode. The detectors are aligned on the gantry opposite to and within a trajectory of the x-ray source.

In additional aspects, the system may further include a sensor monitoring an operational state of the x-ray source in the microbeam radiation therapy mode, and a safety switch operatively connected to the x-ray source and in communication with the sensor. The safety switch is configured to automatically shut down the x-ray source in response to the operational state exceeding a pre-determined threshold.

In aspects, the operational state is one of an operating temperature of the x-ray source and a time of continuous operation of the x-ray source.

In other aspects of the system, a position of the bed is adjustable horizontally along the axis of rotation and laterally thereto, and is also adjustable up and down along a vertical axis, and angularly around the vertical axis.

The microbeam radiation mode of the system may include a stationary mode of operation for MRT, wherein the gantry is rotated to a fixed stationary position to irradiate the targeted portion.

In aspects, the targeted portion corresponds to a portion of a spinal cord. In one aspect, the multi-slit collimator may be mounted to the bed and adjustably positioned along a central axis of the bed. The bed and the multi-slit collimator are adjustably positioned to irradiate the targeted portion of the spinal cord with the microbeams.

The bed, in aspects of the system, includes a headrest that may have a width narrower than a body-resting portion of the bed. The bed may also be tapered in thickness at its lateral edges.

In another aspect of MRT operation, the multi-slit collimator may be aligned to generate the microbeams in planes perpendicular to the axis of rotation, the system being further configured to deliver the array of microbeams continuously over a predetermined angle of rotation of the gantry, and to dynamically adjust the beam-shaping collimator to correspond to a shape of the targeted portion intercepted by the x-ray source over the predetermined angle of rotation.

In yet another aspect of MRT operation, the multi-slit collimator may be aligned to generate the microbeams in planes parallel to the axis of rotation, the system being further configured to deliver the array of microbeams in step-wise adjacent irradiation exposures over a rotation of the gantry over a predetermined range of angles, and to adjust the beam-shaping collimator to correspond to a shape of the targeted portion intercepted by the x-ray source at each step-wise adjacent irradiation angle.

The microbeams in the array, in aspects, may have a thickness in a range of between about 20 microns to about 1 millimeter, and a center-to-center spacing of between 2 to 10 times the thickness.

In other aspects, the x-ray source may be a rotating anode source operating between about 70 kVp to about 150 kVp and having a spot size between about 0.2 mm to about 1.0 mm.

The present disclosure is also directed to a method for delivering microbeam x-ray radiation therapy to a subject. The method includes: providing an x-ray source positioned on a gantry of a computed tomography scanner and a bed for positioning a subject; generating tomographic images of an axial section of the subject; locating a targeted portion of the axial section for microbeam x-ray radiation therapy based on the tomographic images; and delivering therapeutic microbeam x-ray radiation to the targeted portion, using the x-ray source of the computed tomography scanner.

In aspects, the therapeutic microbeam x-ray radiation is delivered by: mounting a multi-slit collimator downstream of the x-ray source to generate an array of microbeams; positioning the bed to position the targeted portion within a trajectory of the array of microbeams; and operating the gantry to deliver the therapeutic microbeam x-ray radiation to the targeted portion.

The method may further include operating the gantry in one of a stationary, continuous, and step-wise mode.

In additional aspects, the method may include removably mounting the multi-slit collimator and a beam-shaping collimator to the gantry, wherein the beam-shaping collimator is fixedly positioned upstream of the multi-slit collimator, the multi-slit collimator and the beam-shaping collimator rotating with the x-ray source on the gantry.

In aspects, the method may include: aligning the multi-slit collimator to generate the microbeams in planes parallel to an axis of rotation of the gantry; and operating the gantry in a step-wise mode. In this mode, the method may include delivering the array of microbeams to the targeted portion in step-wise adjacent irradiation exposures over a rotation of the gantry over a predetermined range of angles, and adjusting the beam-shaping collimator to correspond to a shape of the targeted portion intercepted by the x-ray source at each step-wise adjacent irradiation angle.

In aspects, the method may include: aligning the multi-slit collimator to generate the microbeams in planes perpendicular to an axis of rotation of the gantry; and operating the gantry in a continuous mode. In this mode, the method may include delivering the array of microbeams continuously over a predetermined angle of rotation of the gantry, including dynamically adjusting the beam-shaping collimator to correspond to a shape of the targeted portion intercepted by the x-ray source over the predetermined angle of rotation.

The targeted portion, in aspects, may be part of a brain or a whole brain or a spinal cord, the method including a treatment protocol for treating disease or injury of the brain or spinal cord.

In some aspects, the targeted portion is a portion of a spinal cord and the gantry includes operating the gantry in a stationary mode. In this mode, the method includes rotating the gantry to fixedly position the x-ray source beneath the bed to direct the x-ray source upward at the targeted portion, and removably mounting the multi-slit collimator to the bed and within a trajectory of the x-ray source to deliver the array of microbeams to the targeted portion.

In addition to the above aspects of the present disclosure, additional aspects, objects, features and advantages will be apparent from the embodiments presented in the following description and in connection with the accompanying drawings.

BRIEF DESCRIPTION OF THE DRAWINGS

The drawings constitute a part of this disclosure and include examples, which may be implemented in various forms. It is to be understood that in some instances, various aspects of the disclosure may be shown exaggerated or enlarged to facilitate understanding. The teaching of the disclosure can be readily understood by considering the detailed description in conjunction with the accompanying drawings, which are briefly described below.

FIG. 6 represents embodiments of methods of the present disclosure for delivering microbeam x-ray radiation therapy to a subject.

FIG. 7 represents an additional embodiment of the present disclosure for delivering microbeam x-ray radiation therapy to a subject.

FIG. 8 represents yet another embodiment of the present disclosure for delivering microbeam x-ray radiation therapy to a subject.

The various aspects of the present disclosure mentioned above are described in further detail with reference to the aforementioned figures and the following detailed description of certain embodiments.

DETAILED DESCRIPTION

The following detailed description of embodiments in the present disclosure are made with reference to the accompanying drawings. It should be apparent to those skilled in the art that the described embodiments provided herein are illustrative only and not limiting, having been presented by way of example only. All features disclosed in this description may be replaced by alternative features serving the same or similar purpose, unless expressly stated otherwise. Therefore, numerous other embodiments of the modifications thereof are contemplated as falling within the scope of the present disclosure as defined herein and equivalents thereto. In the following description, detailed explanations of related well-known functions or features known in the art are omitted to avoid obscuring the embodiments of the disclosure with unnecessary detail.

Both a system and a method are provided in this disclosure. In the detailed description that follows, it should be noted that while additional method steps may be incorporated in the description and figures of the details of embodiments of a system, which are not explicitly identified as such in functional diagrams of exemplary methods, such method steps are still considered to be disclosed steps of embodiments of methods within the scope of the present disclosure.

The present disclosure is directed to a method and system for utilizing an x-ray tube mounted on a computed tomography ("CT") scanner to clinically administer x-ray microbeams to a patient. Embodiments of a method and system for performing microbeam radiation therapy ("MRT") using an x-ray source of a CT scanner are provided that can minimize damage of healthy tissue proximal to a targeted portion, and also minimize damage of healthy tissue that can otherwise occur in conventional systems that require repositioning of a patient, or subject, for radiation therapy, after a diagnostic computed tomography imaging scan.

It should be understood that though the term "patient" is used in the description of the various embodiments, the term "patient" is not intended to limit the methods and systems of the disclosure, which are applicable to any subject, including to so-called "patients."

Figure 2:
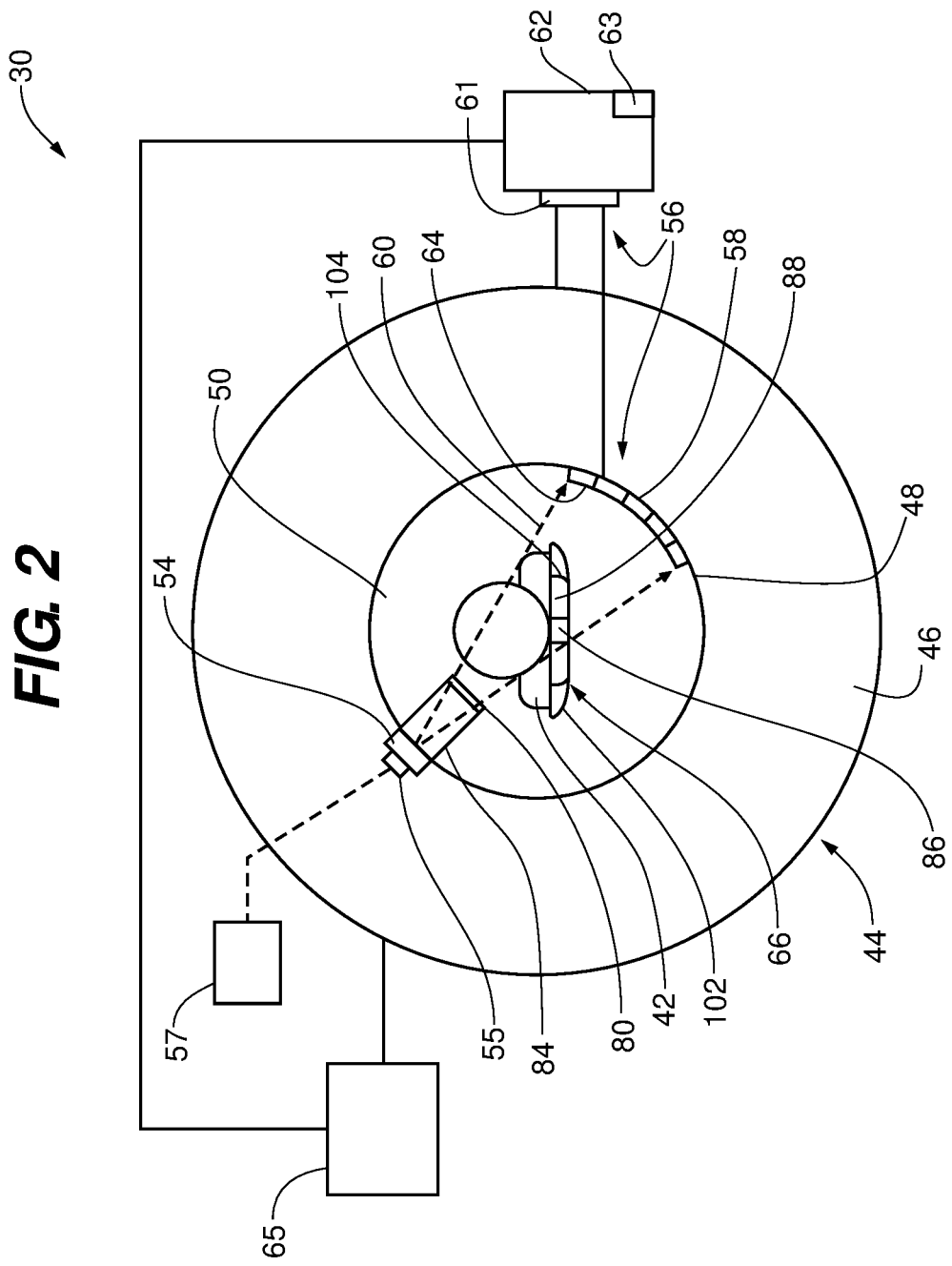
FIG. 2 is a schematic and pictorial representation of an embodiment of a system of the present disclosure, showing a front-end view of a portion of the system.

One embodiment of a system 30 of the present disclosure for dual-use CT scanner and MRT is shown in FIG. 2. As further described herein, the system and methods of the disclosure allow MRT from a wide range of angles, and prompt switching between CT and MRT modes of operation with a patient staying in the same position. Accordingly, the disclosed system and method of the disclosure provide a modality for combining CT imaging and MRT, which allows for imaging, targeting, and therapy over a wide range of imaging and therapy configurations to be carried out all at the same imaging/therapy session.

Figure 3:
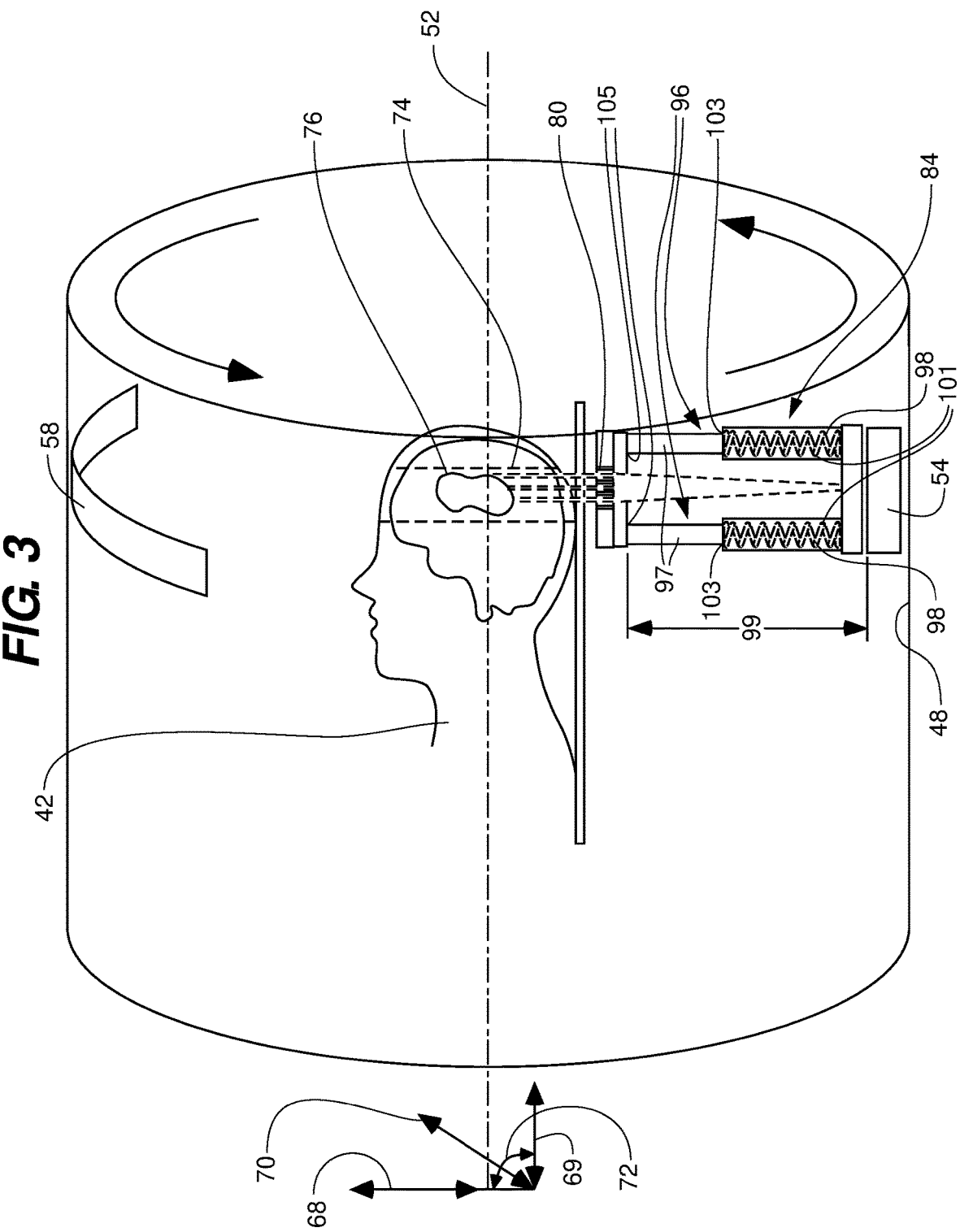
FIG. 3 is a pictorial representation of an embodiment of the system of the present disclosure aligned for microbeam radiation therapy of the brain of a subject.

It should be noted that CT imaging will be very useful in any therapy application even if the characteristics of a soft tissue lesion being targeted for therapy does not allow its delineation with the CT scanner. This is because CT can often display certain non-soft-tissue anatomical landmarks surrounding the lesion, which are useful in targeting the lesion. Referring for example to FIG. 3, in this way, the system 30 can be implemented to use the CT images acquired in the CT scanning mode for an axial section 74 of a patient 42 to identify and localize the target, referred to herein as the "targeted portion" 76, in preparation for administration of the microbeam irradiation and therapy in the MRT mode. In implementing the system and methods of the present disclosure, the resulting quality of patient positioning and targeting are enhanced over prior art systems, by using the same patient (or subject) position for imaging and therapy. The accuracy of targeting and patient positioning may be especially important when implementing the thin microbeams used in microbeam radiation therapy.

"Microbeam radiation therapy" or "MRT" is a phrase that has been used in the prior art to describe high energy x-ray radiation that is delivered to a subject in an array of parallel, or substantially parallel, thin planes of x-rays, formed by segmenting a solid beam of radiation from a high-energy synchrotron source. Most of these synchrotron studies have been performed for two thickness ranges of microbeams segmented from the solid synchrotron beam: less than or equal to about 300 μm (~0.3 mm), or from 300 to 700 μm. It has been shown in these synchrotron studies that these particular synchrotron-generated microbeams, having thicknesses below 700 μm and separated sufficiently to maintain a low valley dose between adjacent microbeams, have clinical value based on a "tissue-sparing effect."

The tissue-sparing effect of arrays of microbeams of less than 700 μm has been demonstrated using synchrotron high energy radiation, with a large number of experiments carried out with synchrotron-generated x-rays at the National Synchrotron Light Source (NSLS), Brookhaven National Laboratory (BNL), and at the European Synchrotron Radiation Facility (ESRF) in Grenoble, France. The first synchrotron study using microbeams of less than 700 microns was carried out at the NSLS in the early 1990s, and was comprised of a single exposure of the rat cerebellum to an array of parallel, 37-μm thick planes of synchrotron x-ray microbeams, spaced 75 μm on center, at triplet beams of 250 Gy and 1,000 Gy in-beam, in-depth. At three months after the single exposure, there was no visible damage with 250-Gy microbeams, while the only damage observed with the 1,000-Gy irradiations was the disappearance of the granular cells in the direct path of each microbeam, without causing any general tissue necrosis. About 15 years later it was further shown at the NSLS in studies on the rat spinal cord and brain that x-ray microbeams as thick as 0.68 mm still retained much of their tissue-sparing effect.

Based on similar studies of the tolerance of a rat brain exposed to 170 Gy of synchrotron-generated microbeam radiation using 0.68 mm thick planar microbeams, it has been suggested that the tolerance advantage of arrays of 0.68 mm microbeams over solid x-ray beams in the rat brain may be at least a factor of 8:1, and most probably closer to 10:1.

Although the radiobiological mechanisms of the tissue-sparing effect of various thickness ranges of microbeams are still an area of ongoing study, it has been proposed that the two mechanisms that may broadly underlie this tissue-sparing effect are the "dose-volume effect" and the "prompt biological repair effect." The dose-volume effect refers to the observation that the smaller the target, the larger its dose tolerance, and is a well-known principle that is not limited to mm or sub-mm beams. The latter effect, however, is specific to beams with sub-mm dimensions and has been explored in animal studies such as those performed at the NSLS, as described above. It is related to the fast repair of capillary blood vessels from microbeam exposure to synchrotron radiation. Under certain conditions, the exposed capillary blood vessels of a mouse cerebellum have been shown to repair themselves within 12-24 hours.

Applications of MRT using synchrotron radiation have been suggested for oncological and neurological applications, such as the treatment of tumors, spinal cord injury, epilepsy, Alzheimer's disease, and demyelinating diseases including multiple sclerosis and some experiments with animals to treat tumors and other conditions have been tried at several synchrotron facilities around the world. However, no clinical implementations of the methods have been carried out with synchrotron x-rays at least in part because of the logistical issues involved.

In the present disclosure, the inventors exploit the high beam intensity, relative to its source spot size, of the x-ray tube of a Computed Tomography (CT) scanner to provide a system and method of performing microbeam radiation therapy using a CT scanner as described further herein. The method and system of the present disclosure take advantage of the tissue-sparing effect of microbeams to minimize damage to healthy tissue proximal to the intended target of the radiation therapy. In addition, by using the CT scanner for the dual purpose of imaging the patient to identify the targeted region and then performing the microbeam radiation delivery therapy, diagnostic imaging and radiation therapy can be carried out in a single session, without moving the patient to a different device. This eliminates the unnecessary exposure of healthy tissue to the high-energy x-ray radiation that can occur due to patient repositioning errors or mismatches between the diagnostic imaging device and the radiation delivery device.

Figure 1A:
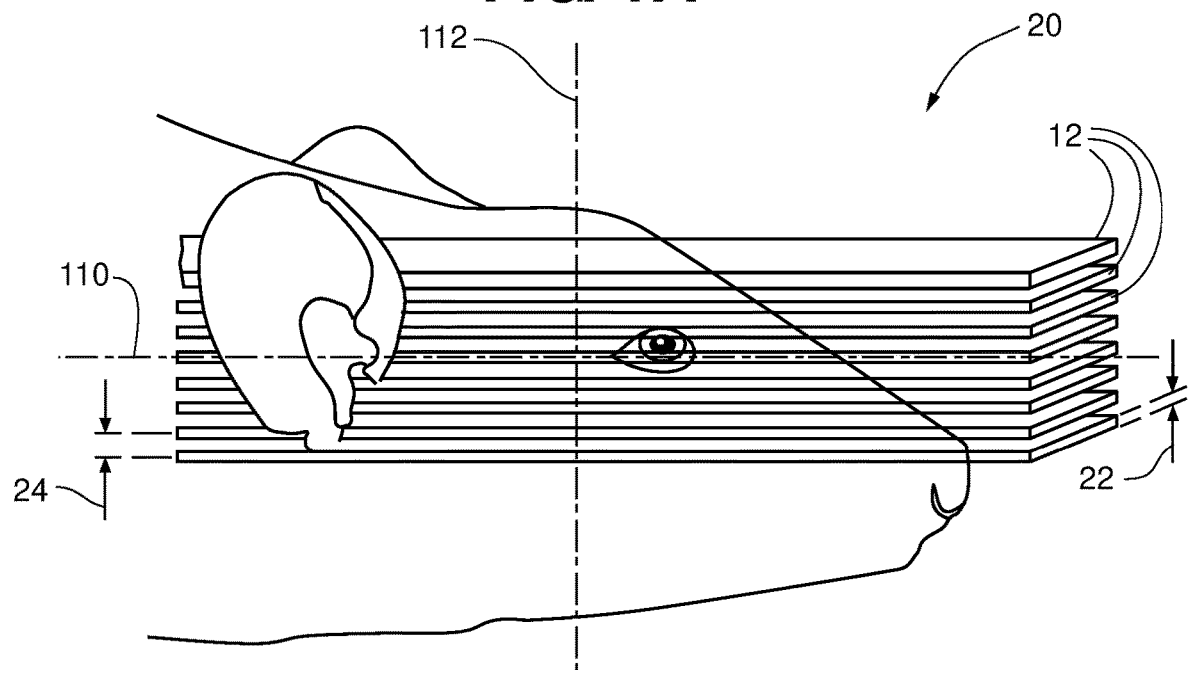
FIG. 1A is a pictorial representation of an array of evenly spaced, parallel, x-ray microbeams irradiating a rat over its head.
Figure 1B:
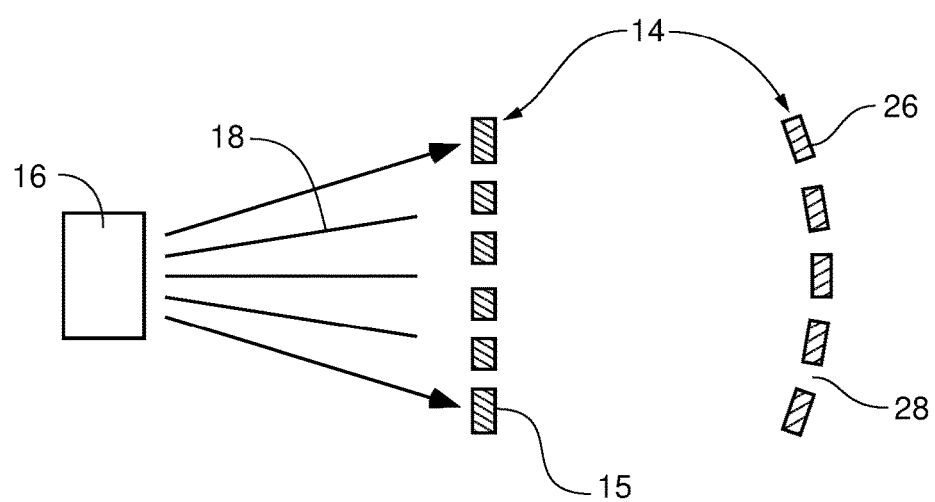
FIG. 1B is a pictorial representation of embodiments of multi-slit collimators of the disclosure.

Referring to FIGS. 1A and 1B, microbeams 12 are thin, parallel or substantially parallel, planar beams of radiation, which are generated by positioning a multi-slit collimator 14 in the path of an x-ray source 16 of a solid beam 18. In this configuration, an array 20 of the microbeams 12 can be generated, each microbeam being characterized by a beam thickness 22 and adjacent microbeams being spaced apart by a center-to-center ("on-center") spacing 24.

As further described herein, in the system and methods of the present disclosure, the multi-slit collimator is removably mounted for MRT in the path of the x-ray source of a CT scanner and in a position close to the body of the patient, and in embodiments, as close as possible to the body.

Embodiments of the multi-slit collimator 14 of the present disclosure, as shown in FIG. 1B, may be constructed from a flat plate 15.

In embodiments, the multi-slit collimator 14, as shown in FIG. 1B, may be constructed from a rounded, or cylindrical block 26. Suitable multi-slit collimators may also include flared slits 28 to accommodate the diverging beam 18 of the x-ray source 16 of the disclosure. As shown in FIG. 2, in the embodiments of the system 30 of the disclosure, the multi-slit collimator 14 is also a removably mounted multi-slit collimator 80, being removably mounted in the path of the x-ray source 54 of a CT scanner 44 for dual use of the system 30 for MRT.

The x-ray source 16, in embodiments, is an x-ray source 54 (see FIG. 2) in a computed tomography (CT) scanner. The x-ray source may be a rotating anode of an x-ray tube, or any other suitable x-ray source. In embodiments, the x-ray source 54 of the system of the disclosure is capable of producing x-rays of sufficient high beam intensity from a suitably small spot size to be useful for both CT imaging and radiation therapy.

For example, in some embodiments, the x-ray source 54 produces x-rays of energies between about 70 kVp to about 150 kVp, and has a spot size, in embodiments, between about 0.2 mm to about 1.0 mm.

In other embodiments, the x-ray source 54 may be a line focus x-ray tube (LFXT), which produces a line focus. These sources are capable of increasing the beam brilliance by more than two orders of magnitude when compared to conventional x-ray tubes. In embodiments, the LFXT may have up to one cm focal spot or line, with focal spot widths of between about 20 microns and about 500 microns.

It should be noted that while certain operating parameters, such as spot size and operating x-ray energy in kVp, of some known x-ray sources are disclosed herein, along with corresponding in-beam doses produced using certain x-ray sources and beam parameters, the scope of this disclosure is not limited thereto.

Any suitable source for CT imaging can be used in the embodiments shown in FIGS. 2-5, which is also capable of sufficient dose for MRT operation. For example, as mentioned supra, in embodiments, the x-ray source 54 may be any LFXT known in the art configured for both CT and radiation therapy. As one of skill in the art will recognize, the detectors 58 and other elements of the image apparatus 56 described further herein may be appropriately modified in accordance with methods known in the art to accommodate imaging and reconstruction to generate tomographic images using a line focus rather than a spot focus.

Figure 4:
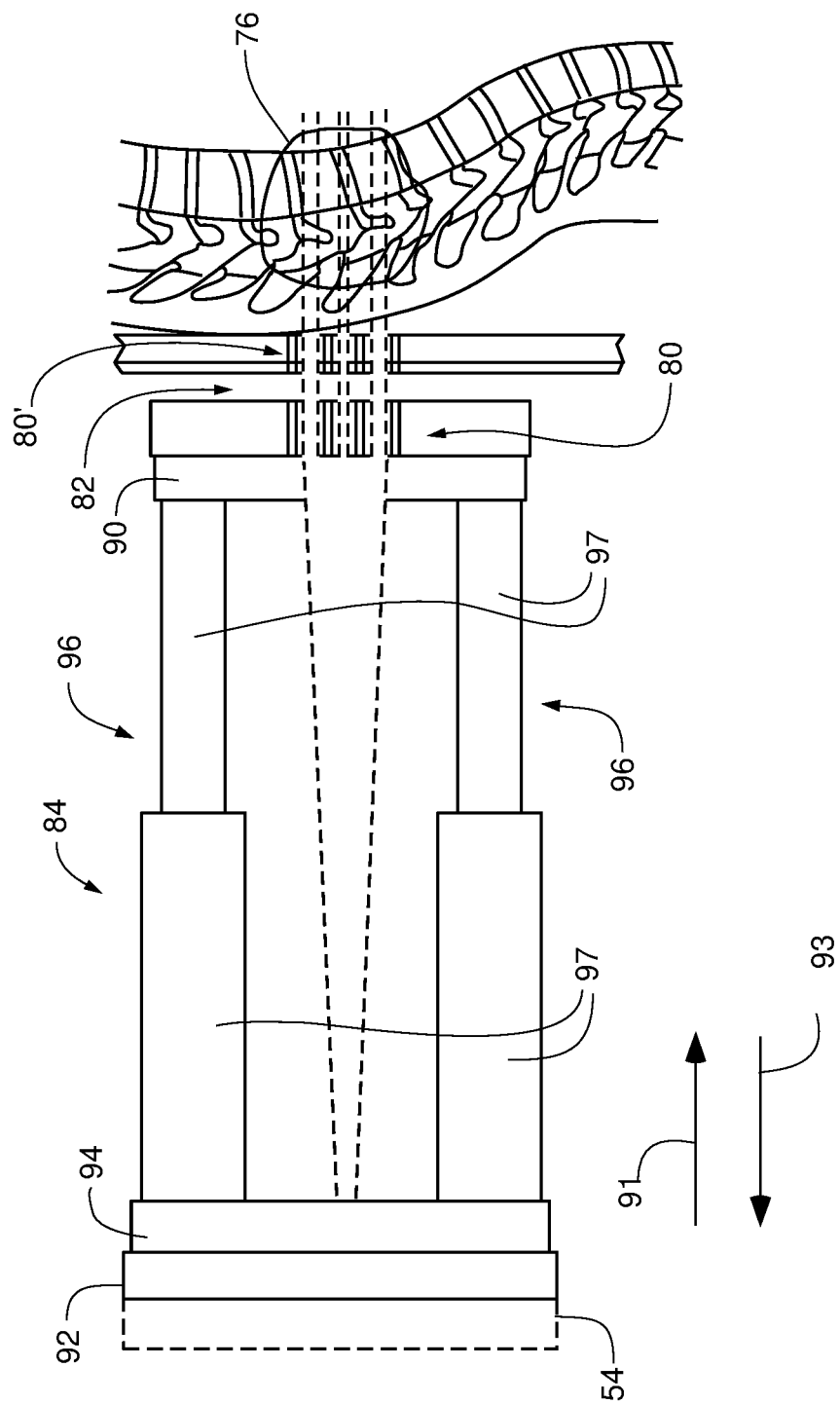
FIG. 4 is a pictorial representation of an embodiment of a multi-slit collimator removably mounted downstream of an x-ray source in an embodiment of the system.

In addition, as described herein in reference to FIG. 4, suitable beam filters 94 may be inserted for use in the CT mode, as necessary, to accommodate the x-ray source 54 of the system 30 to insure safe and accurate imaging of the patient in CT mode. Different beam filters 94 may then be substituted for operation in the MRT mode.

In embodiments, the x-ray source 54, which may be an LFXT source, may have up to one cm focal spot or line, with focal spot widths of between about 20 microns and about 500 microns, and in-beam dose rates between about 10 to 200 Gy/s depending on the focal spot width and the shape of the beam produced. In certain embodiments, cooling elements may also be provided to cool elements of the x-ray source such as the cathode, and/or the microbeam/minibeam collimator during operation.

It will also be appreciated that in certain embodiments wherein the x-ray source 54 is characterized by a line focus, for example, an LFXT tube, the line focus of the x-ray source 54 is preferably aligned with the plane of the slits of the multi-collimator 80. In further embodiments, the x-ray source 54 will also be rotatable with the multi-slit collimator 80 when switching between parallel and perpendicular modes of MRT operation, as described further herein, to maintain the relative position of the line focus to the planes of the multi-collimator 80 slits when operating in the different MRT modes.

In other embodiments shown in FIGS. 9A and 9B, which are discussed further below, the MRT source 254 is different than the CT source 54. In these embodiments, the second x-ray source 254 may be any suitable x-ray source regardless of its suitability for CT imaging, i.e., regardless of its spot size or shape and divergence, and may include, but is not limited to, an orthovoltage x-ray source or a LFXT.

Referring to the geometry of an embodiment of a microbeam array 20 as shown in FIG. 1A, in embodiments of the disclosure, microbeam arrays may be formed of a number of microbeams 12 in a range of between 2 to 10 microbeams.

In embodiments, the thickness 22 may be in a range of between 20 microns and 1 millimeter, in particular embodiments, between 20 microns and 700 microns.

In other embodiments, the thickness 22 may be in a range of between 20 microns and 300 microns.

In additional embodiments, the thickness 22 of the microbeams may be in a range of between about 0.2 mm to 0.5 mm thick.

In yet additional embodiments, the thickness 22 of the microbeams is about 0.3 mm.

In still additional embodiments, the thickness 22 of the microbeams is between about 0.3 mm and 0.7 mm.

In embodiments, the beam spacing on-center 24 may be in a range of between about 0.6 mm and 1.2 mm.

In other embodiments, the beam spacing on-center may be in a range of between about two-times the thickness 22 of the microbeams in the array to about ten-times the thickness 22 of the microbeams in the array.

In embodiments of the disclosure using the x-ray source of a CT scanner, in-beam, incident microbeam doses may range from about 40 Gy to about 160 Gy.

In-beam microbeam doses in a range sufficient to ablate certain mitotic cells, e.g., endothelial cells and tumor cells, between 40 Gy and 160 Gy in embodiments, are administered to a patient in accordance with particular methods of the present disclosure for the treatment of tumors.

Referring to FIG. 2, an embodiment of a system 30 of the present disclosure for delivering therapeutic microbeam x-ray radiation to a patient 42 includes a computed tomography ("CT") scanner 44. In embodiments, the computed tomography scanner 44 may be any suitable CT scanner 44 used to produce tomographic images of axial sections through a patient.

The computed tomography scanner 44 includes a gantry 46, which may be of annular construction, and which includes an inner surface 48 surrounding an opening 50 in which the patient 42 is positioned for diagnostic imaging. Referring also to FIG. 3, for example, the computed tomography scanner 44 is further characterized by an axis of rotation 52 around which the gantry 46 rotates.

The computed tomography scanner 44 also includes a source, e.g., x-ray source 54, mounted to and rotatable with the gantry 46, and imaging apparatus 56. In embodiments, the x-ray source 54 is a rotating anode type x-ray source.

The imaging apparatus 56 of the computed tomography scanner 44 for CT operation includes detectors 58, which are mounted to the gantry 46 at a location on the gantry 46 to intercept a trajectory of the x-ray source beam 60, for example, at a position on the gantry 46 diametrically opposite the x-ray source 54.

In embodiments, the detectors 58 are rotatable with the gantry 46 so that the detectors 58 remain aligned to the x-ray source beam 60 for generating tomographic images.

In other embodiments, when the CT scanner 44 is operated in a CT imaging mode, the detectors remain aligned to the x-ray source beam 60, and when the CT scanner is operated in a microbeam radiation therapy (MRT) mode, the detectors 58 can be decoupled from rotating with the gantry 46, to remove them from the trajectory of the x-ray source 54 for MRT to protect them from unnecessary prolonged exposure to radiation.

The system 30 may also include a shutter 64, formed of an x-ray absorbing material, e.g., a metal plate, that may be positioned to cover a front of the detectors 58 when operating in the MRT mode.

In embodiments, the shutter 64 may be automatically positioned in place over the detectors 58 when the system is switched to the MRT mode of operation.

The system 30, as shown in FIG. 2, may also include, particularly for operation in the MRT mode, a sensor 55 that monitors an operational parameter indicating an operational state of the x-ray source 54. A safety switch 57 operatively connected to the x-ray source and in communication with the sensor 55 is configured to automatically shut down the x-ray source 54 in response to the operational parameter exceeding a pre-determined threshold. For example, sensor(s) 55 for monitoring an operating temperature of the x-ray source 54 and/or a time of continuous operation of the x-ray source 54 together with circuitry (safety switch 57) can cause the x-ray source 54 to shut the beam automatically when the heat load in the anode is extended above a certain threshold or beyond a certain time limit. This can protect the x-ray tube from damage that might occur from high power and lengthy exposures that surpass the anode's heat tolerance and intensity limit.

The imaging apparatus 56 for diagnostic CT imaging, as those of skill in the art will appreciate, also includes data acquisition controllers 61 and computer processing hardware including processors 62 operatively connected to the detectors 58 to collect and process the detector data, which is collected as a function of rotational angle of the gantry 46, for each axial "slice." The imaging apparatus 56 also includes software 63 configured for execution by the processors 62 to generate the reconstructed axial slice images over an axial thickness for which detector data is acquired.

Referring still to FIGS. 2 and 3, the system 30 also includes a bed 66 on which the patient 42 is positioned.

The bed 66 is motorized to allow controlled movement, using any suitable motors and controllers known in the art, in multiple directions. For example, the translation of the bed 66 in a horizontal direction into and out of the opening 50 may be controlled by an operator of a computer system 65 configured to control the operation of the system 30 for both CT imaging and MRT. In embodiments, the bed 66 is positionable in one or more directions by the operator prior to CT scanning and/or MRT.

In addition to providing the functionality of operator-guided control of certain aspects, e.g., of the position of the bed 66 in the system 30, the computer system 65 in embodiments preferably includes a control module that also allows automated switching to different modes of operation. The control module may include processor(s) preferably configured, according to methods known in the art, to communicate with the controllers and motors of the various moving and/or operable parts of the system 30, including the rotation of the gantry 46, positioning of the bed 66, operation of the shutter 64, and of the x-ray source 54 in the system 30. The processor(s) are further configured to implement executable program steps to operate the various moving and/or operable parts in automated and switchable modes of operation. For example, the control module of the computer system 65 is configured, in embodiments, to operate in a CT scanner mode, and to switchably operate in MRT mode, for example, in response to user input. When switched to the MRT mode, in one embodiment, the shutter 64 is automatically positioned in place to cover the detectors 58 of the CT scanner 44.

The computer system 65 and control module may also be configured to automatically position and operate the gantry 46 and/or bed 66 in accordance with any one of a selected mode of operation for MRT, as described herein, such as a stationary mode, continuous mode, and step-wise mode. As one of skill in the art will appreciate, additional user input may be needed, and parameters selected, in accordance with the particular application of MRT.

Referring to FIG. 3, the bed 66 is preferably configured to be adjustably positioned in a vertical direction 68, as well as translated in a direction parallel 69 to the rotation axis 52, or horizontally. In embodiments, the bed 66 is also configured to be adjustably positioned laterally 70 to the rotation axis 52, for treating targets with MRT that are located away from the body's midline, or central median plane. In further embodiments, the bed 66 is configured to be positioned angularly around the vertical axis 68, for irradiating the brain, for example, with microbeam planes not axial to the patient's body.

The bed may be moved along one of the axes during MRT. For example, depending on the size of the target along the axis of rotation 52 of the CT scanner 44, the bed 66 may be moved stepwise in direction 69, during separate irradiation, to assure exposure of the axial extent of the target.

Referring to FIGS. 2-4, the system 30 for delivering MRT to a patient further includes a multi-slit collimator 80 removably mounted downstream 91 of the x-ray source 54, to deliver an array 82 of microbeams of therapeutic x-ray radiation to the targeted portion 76 of the axial section 74 (as shown in FIG. 3) imaged by CT scanning, without repositioning the patient to a different machine.

As shown in FIGS. 2-4, for example, the multi-slit collimator 80 can be removably mounted, for example, via a mounting assembly 84, to the gantry 46. The mounting assembly 84 may be removably mounted, for example, via attachment directly to the gantry 46, e.g., to the inner surface 48 of the gantry 46 or via attachment to the housing of the x-ray source 54, using any suitable attachment devices. The mounting assembly 84 is configured to maintain the multi-slit collimator 80 in position within the trajectory of the x-ray source beam 60.

Referring to FIG. 4, the removable mounting assembly 84 may also include a beam-shaping collimator 90 located upstream 93 of the multi-slit collimator 80 for shaping the beam to conform to the overall shape of the target at a particular irradiation angle. Additional beam-altering components may include one or more of the following, which may in the following order going away from the x-ray source 54: a bow-tie filter 92, a beam filter such as a beam energy filter 94, which is chosen for the particular application of MRT, and the beam-shaping collimator 90.

In embodiments, the beam-shaping collimator 90 is a multi-leaf collimator. In additional embodiments, the collimator 90 is made of tungsten, tungsten alloys, or other heavy metal alloys. The leaves, in embodiments, may be independently electronically movable to allow automatic adjustment and dynamic re-shaping of the collimator 90 for each irradiation angle during MRT.

As shown in FIGS. 3 and 4, the removable mounting assembly 84 includes positioning or spacing elements 96 positioned between the x-ray source 54 and the multi-slit collimator 80, which may include rods 97, in embodiments, for maintaining the multi-slit collimator 80 at a distance 89 from the x-ray source 54. The positioning elements 96 may be of a fixed length. For rotational modes of MRT, the positioning elements 96 must be adequately short enough to accommodate the bed 66 on rotation over 360 degrees. This means, however, that the multi-slit collimator 80 may not be able to be positioned in the closest proximity to the patient as it is rotated with the gantry, and may be positioned about 2 cm away, depending on the thickness of the bed's head rest.

As shown FIG. 3, the positioning elements 96, in certain embodiments, may include rods 97 and spring-loaded junctions 98 or other flexible-types of joints between the multi-slit collimator 80 and the x-ray source 54. For example, as shown in FIG. 3, if upon rotation of the gantry 46, a distal end of the mounting assembly 84 contacts the bed 66, the spring-loaded junctions 98 allow the length of the mounting assembly 84 i.e., a distance 89 between the multi-collimator 80 and the x-ray source 54, to shorten. In the embodiment shown, each spring-loaded junction 98 is formed from a coiled spring 101 operatively connecting the multi-slit collimator 80, e.g., a first end 103 of one of the rods 97, to the x-ray source 54. A second end 105 of each one of the rods 97 is operatively connected to the multi-slit collimator 80.

Figure 5:
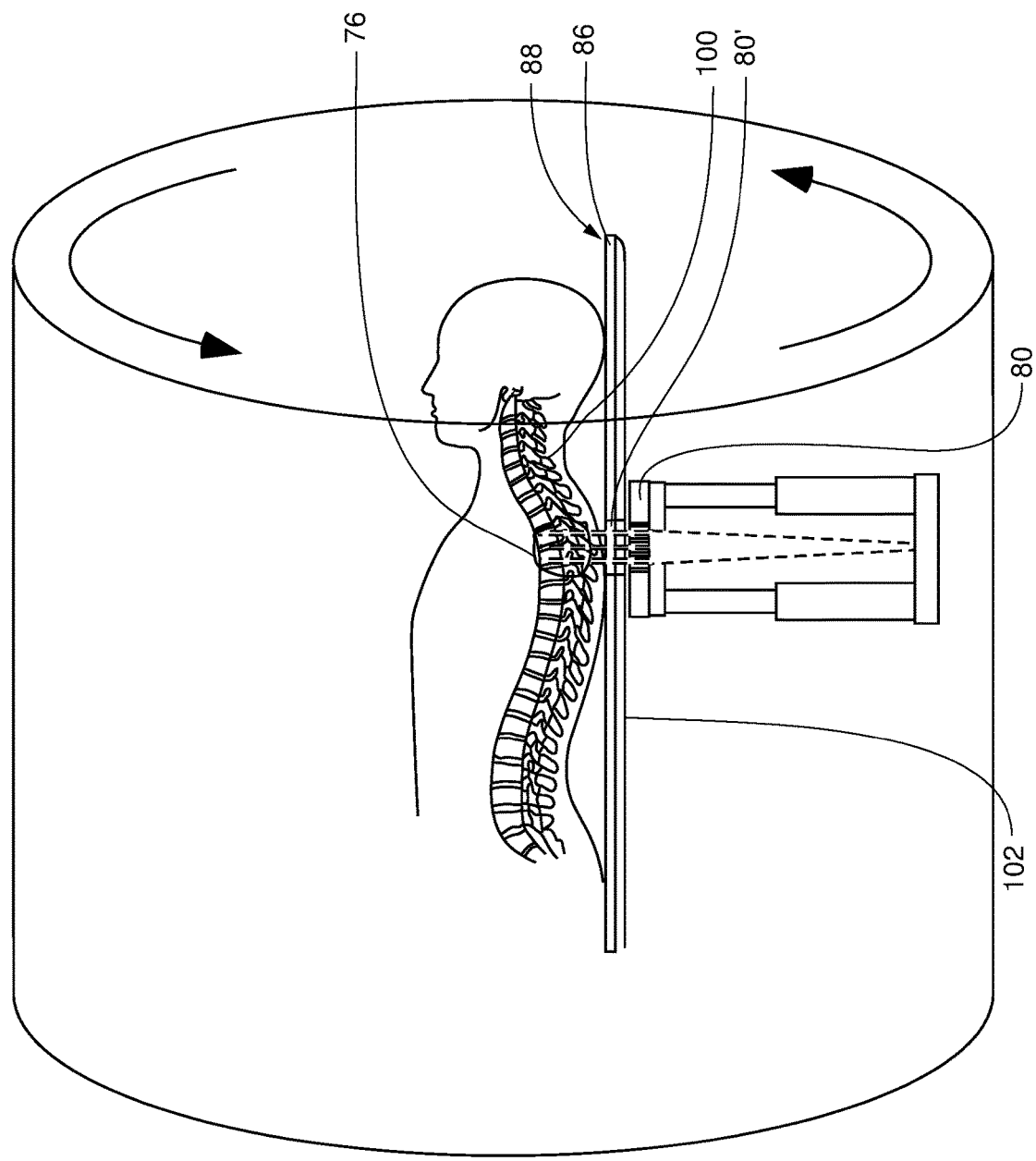
FIG. 5 is a pictorial representation of an embodiment of the system of the present disclosure aligned for microbeam radiation therapy of the spinal cord of a subject.

FIGS. 4 and 5 exemplify a stationary mode operation of the gantry 46, which may be implemented, for example, for a particular application of MRT to the spinal cord as further described herein. The positioning elements 96 shown in FIGS. 4 and 5 are of fixed length.

As shown in FIG. 2, in embodiments, the bed 66 may be configured to removably mount the multi-slit collimator 80 to the underside of the bed 66, which may be particularly useful when delivering MRT to the spine. In this case, the system 30 may be switched to a "stationary mode," with the gantry 46 rotated to a position such that the x-ray source 54 irradiates the spine from below the bed 66, i.e., vertically upward, or substantially vertically upward, as shown in FIG. 5.

Although FIG. 5 shows the multi-slit collimator 80 mounted to the gantry 46 via mounting assembly 84, the multi-collimator 80', also shown in FIG. 5, and as best shown in FIG. 4, can alternatively be mounted directly to the bed 66 for the stationary mode. For example, the bed 66 may include a slot 86 aligned along the axis of rotation 52 and accessible from a headrest end 88 of the bed 66 as shown in FIG. 2. The slot 86 is centered to the central longitudinal axis of the bed 66, parallel to the axis of rotation 52, and also to a central median plane of a patient properly positioned on the bed 66, and, therefore, with the patient's spinal cord. When operating in this mode for spinal MRT, the multi-slit collimator 80' may be inserted into the slot from the headrest end 88 and positioned, e.g., via an actuator under computerized control, under a targeted portion 76 of the patient's spinal cord 100 for MRT in a stationary mode of operation.

Referring still to FIGS. 2 and 5, the bed 66 for performing the methods of the present disclosure is preferably as thin as possible and of a material transparent, or substantially transparent to, the x-ray source 54. The headrest end 88, as may be best seen in FIG. 2, is preferably narrower in width along the lateral direction 70 to the axis of rotation 52 to the gantry (see FIG. 2) than a lower portion 102 that supports the body, and may be in the shape of an oval. In embodiments, the bed is further tapered in thickness at its lateral edges 104. The tapered edges 104 further facilitate the positioning of the multi-slit collimator 80 as close as possible to the patient, particularly, as close as possible to the headrest for 360-degree irradiations of the brain for whole brain MRT treatment, or for partial brain MRT over angles that will rotate the collimator 80 to the side of and beneath the bed 66. These and other applications are described in more detail below.

As will be further understood in the discussion below of methods and applications using the system of the present disclosure, for different applications of MRT, the multi-slit collimator 80 may be positioned to align the planar microbeams parallel to the rotation axis 52 or perpendicular to the rotation axis 52. By way of illustration, referring to FIG. 1A, if the rotation axis is horizontal disposed along an axis 110 of FIG. 1A, then the microbeams are aligned parallel to the axis of rotation. On the other hand, if the rotation axis is vertically in FIG. 1A along an axis 112, then the microbeams shown in FIG. 1A are aligned perpendicular to the axis of rotation 112.

The system 30 of dual-use CT and MRT of the present application permits a wide variety of MRT schemes and parameters. For example, in embodiments of the system and methods described herein, the multi-slit collimator 80 may be rotatably positioned in either the parallel or perpendicular orientation to the axis of rotation 52, depending on the particular MRT application.

Referring to FIG. 6, as well as to FIGS. 2-5, embodiments of methods of the disclosure using an embodiment of the system 30 described herein, include generating CT images, at 120, of an axial section 74 of the patient 42, using the CT scanner 44, e.g., and locating a targeted portion 76 of the axial section 74 for therapeutic x-ray radiation based on the CT images, at 122. The method also includes delivering therapeutic microbeam x-ray radiation to the targeted portion 76, at 124, by, in embodiments: mounting a multi-slit collimator downstream and in the trajectory of the x-ray source beam 60 to generate an array of microbeams, at 126, positioning the bed to irradiate the targeted portion, at 128, and operating the gantry 46 to deliver the MRT to the targeted portion 76, at 130.

In addition to the stationary mode described above with particular reference to FIG. 5 and to treatment of the spinal cord 100, the system 30 may be operated in a rotational mode, which may be either in a continuous mode or in a step-wise mode, as further described below for various applications. Referring to FIG. 6, for example, in further embodiments of a method of the disclosure, to carry out MRT in one of a stationary, continuous, or step-wise mode, the gantry 46 is operated in one of a stationary, continuous, and step-wise mode, at 132.

In embodiments of the methods of the disclosure the targeted portion 76 is part of a brain or spinal cord, the method including a treatment protocol for treating disease or injury of the brain or spinal cord.

In additional embodiments, at 136, the method includes removably mounting the beam-shaping collimator 90 in fixed position upstream of the multi-slit collimator 80, both the multi-slit collimator 80 and beam-shaping collimator 90 removably mounted together to the gantry 46, for example, via the mounting assembly 84 shown in FIG. 4. The multi-slit collimator 80 and the beam-shaping collimator 90 remain aligned to the x-ray source 54 with rotation of the gantry 46.

In other embodiments, at 138, the method includes removably mounting the multi-slit collimator 80 to the bed 66, and operating the gantry in the stationary mode, for example, for MRT of the spinal cord. As described supra, in the stationary mode, the x-ray source 54 is rotated to a fixed position underneath the bed 66 to irradiate a portion of the spinal cord 100.

In potential clinical applications of embodiments of the methods and system disclosed herein for delivering microbeam radiation therapy, the following two microbeam exposure alignments are considered. The first is with the microbeam planes perpendicular to the rotation axis 52 of the CT scanner, which are the orientations of the microbeams shown in FIGS. 3-5 (see array 82 in FIG. 4) and the second is with the microbeam planes parallel to the rotation axis. The geometry of the latter is illustrated in FIG. 1A, where the planes of the microbeams 12 are parallel to axis 110.

For the second alignment scheme, in which the microbeam planes of irradiation are parallel to the axis of rotation 52, the exposures are carried out step-wise, with the microbeam exposure being stopped while rotating the x-ray source 54 via the gantry 46 from one irradiation angle to another. This is the step-wise mode of operation referred to supra.

For the irradiations with the microbeam planes perpendicular to the axis of rotation 54, no step-wise exposures are necessary, particularly when the entire angular range, i.e., for a predetermined 360-degree angle of rotation, of the brain are irradiated.

Referring to FIG. 7, with reference also to FIGS. 2-4, embodiments of a method of the present disclosure for performing MRT may include removably mounting the multi-slit collimator 80 and the beam-shaping collimator 90 to the gantry 46, at 136, with the beam-shaping collimator 90 upstream of the multi-slit collimator 80, and aligning the multi-slit collimator 80 to generate the microbeams in planes perpendicular to the axis of rotation 52 of the gantry 46, at 140. The method further includes operating the gantry 46 in a continuous mode, at 142. Continuous mode operation, at 142, may include delivering the perpendicularly-oriented microbeams to the targeted portion 76 in a continuous irradiation exposure, at 144, over a predetermined angle of rotation of the gantry 46, while dynamically adjusting the beam-shaping collimator, at 146, to correspond to the shape of the targeted portion over predetermined angle of rotation.

Referring to FIG. 8, with reference also to FIGS. 2-4, embodiments of a method of the present disclosure for performing MRT include removably mounting the multi-slit collimator 80 and the beam-shaping collimator 90 to the gantry 46, at 136, with the beam-shaping collimator 90 upstream of the multi-slit collimator 80, and aligning the multi-slit collimator 80 to generate the microbeams in planes parallel to the axis of rotation 52 of the gantry 46, at 148. The method further includes operating the gantry 46 in a step-wise mode, at 150. Step-wise operation, at 150, may include delivering the array of microbeams to the targeted portion 76 in step-wise adjacent irradiation exposures, at 152. The irradiation is performed at predetermined angular steps of rotation, over a pre-determined rotation of the gantry 46.

For example, for whole brain scans, the irradiation may be performed over a pre-determined rotation of the gantry 46 of 360 degrees, at predetermined steps of, e.g., 10 degrees. The brain is irradiated only at each angular step, and not during movement of the gantry from one irradiation angle to another. This may be accomplished either by using a shutter over the x-ray source 54 during rotation from one irradiation angle to the next, or by otherwise modulating the x-ray source 54 to turn off x-ray generation when rotating from one step to the next.

At 154, the beam-shaping collimator may also be adjusted to correspond to a shape of the targeted portion 76 intercepted by the x-ray source 54 at each step-wise adjacent irradiation angle.

It should be clear that in any of the applications described herein that implement a rotational mode of MRT, referring, for example, to FIG. 4, the beam-shaping collimator 90, which may be a multi-leaf collimator (MLC), and the multi-slit collimator 80 will be fixed in relation to the x-ray source 54, moving with the x-ray source 54 as it rotates on the gantry. As described herein, they are also removably mounted, so that they may be removed for the process of CT imaging.

Figure 9A:
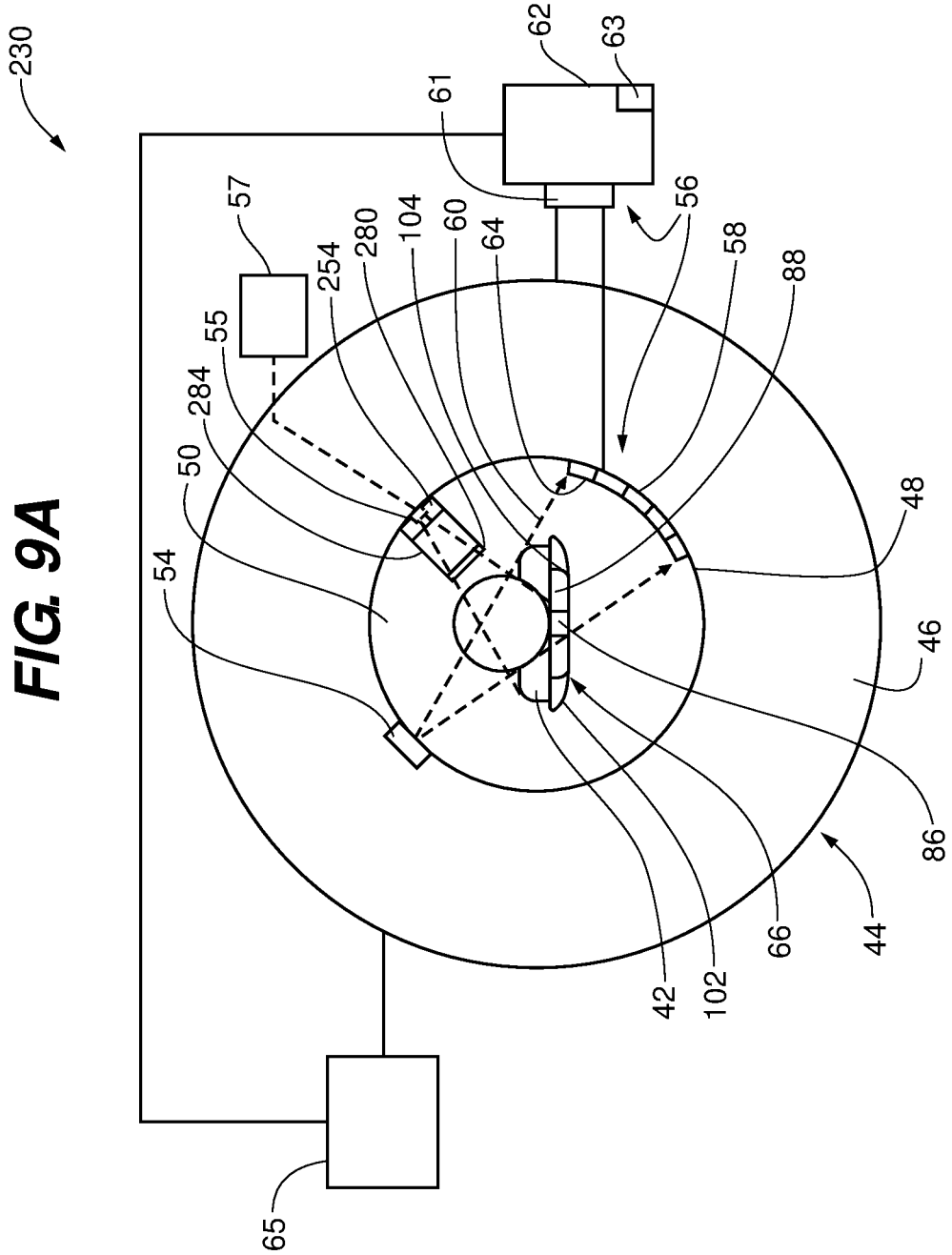

Referring to FIGS. 9A and 9B, in certain embodiments of a system 230 and methods of the present disclosure, a second (MRT) x-ray source 254 may be removably mounted to a second location on the gantry 46 for MRT operation via a suitable mounting assembly 284. A suitable multi-slit collimator 280 is also removably mounted downstream of the second x-ray source 254 for delivering an array 282 of microbeams to the targeted portion 76 of the axial section 74 imaged by the CT scanner 44.

In embodiments, the multi-slit collimator 280 is removably mounted to the gantry 46 along with the second x-ray source 254 via the removable mounting assembly 284, the mounting assembly 284 including both the second x-ray source 254 and the multi-slit collimator 254. The multi-slit collimator 280 and second x-ray source 254 are rotatable with the gantry 46.

In other embodiments, the multi-slit collimator 280' is positioned in the bed 66 for use in the stationary mode for irradiation of the spine as described supra in reference to FIGS. 4 and 5. Like mounting assembly 84, the mounting assembly 284 for use with the second x-ray source 254, may also include one or more of a bow-tie filter 92, a beam filter such as a beam energy filter 94, which is chosen for the particular application of MRT, and beam-shaping collimator 90.

The system 230 is calibrated to accurately locate the irradiation field of the second x-ray source 254 based on the CT data, in accordance with methods known in the art.

When using the second x-ray source 254 to perform MRT as shown in FIGS. 9A and 9B, the second x-ray source 254 may be any commercially available x-ray source regardless of its suitability for CT imaging, i.e., regardless of its spot size and divergence, may provide additional flexibility in the doses that can be generated for MRT and in the applications of the system.

The second x-ray source, in embodiments, may be one of, but is not limited to, an orthovoltage x-ray source or an LFXT.

The system 230 including the second x-ray source 254 may include, in embodiments, any of the features applicable to the x-ray source 54 when operated in MRT mode. For example, the system 230 may include the sensor 55 that monitors an operational parameter that indicates an operational state of the x-ray source 254 in MRT mode, e.g., operating temperature and/or time of continuous operation, with safety switch 57 operatively connected to the x-ray source 254 and in communication with the sensor 55. The x-ray source 254 is automatically shut down in response to the operational parameter exceeding a pre-determined threshold to protect the x-ray tube from damage that might occur from high power and lengthy exposures.

In addition, the system 230 may operate in any of the modes of operation for MRT disclosed herein, and in accordance with the methods of FIGS. 6-8. Embodiments of methods of the present disclosure, referring to the system 230, include the method of FIG. 6 further including, at 124, the microbeam x-rays being delivered to the targeted portion via the second x-ray source 254, which is removably mounted to the gantry 46. In addition, at 126, the multi-slit collimator is removably mounted in the x-ray beam of the second x-ray source 254.

Accordingly, in FIGS. 6-8, at step 136, in embodiments, when removably mounting the multi-slit collimator with the beam-shaping collimator to the gantry, e.g., via mounting assembly 284, the second x-ray source is also removably mounted via the mounting assembly to the gantry 66.

Applications Involving Microbeam Irradiation of the Brain

Whole brain irradiation, in accordance with the methods and system of the disclosure, may be applied for treating diseases of the brain, such as Alzheimer's disease. Irradiation of the entire brain with arrays of parallel microbeams, as described in FIG. 7, for example, may be performed in one or several sessions. As described in FIG. 7 for parallel microbeams, the exposures would be carried out stepwise.

It has been shown in earlier investigations, that irradiation of the brain of a mouse model of Alzheimer's disease with conventional, non-segmented (solid beam) x-rays produces a reduction in the density and size of amyloid plaques and improves the mouse's cognitive function. On the basis of these results, it is believed that irradiating the brains of Alzheimer's patients with x-ray microbeams in accordance with the present system and methods will also provide these benefits to the patient, while additionally minimizing or eliminating the damage caused to healthy tissue using the prior solid beam irradiations. For Alzheimer's treatment, the methods of irradiation provided herein may be applied in one session, or in several sessions in the course of several days using dose fractionated whole brain irradiation. Each exposure will target a certain percentage of the brain volume, based on the brain's distribution of the amyloid plaques.

Alzheimer's may also be treated by irradiation of the entire brain with arrays of perpendicular microbeams, as described in FIG. 8, for example, which may also be performed in one or several sessions.

Whether using parallel or perpendicular microbeam geometry, the multi-slit collimator producing the microbeams should be maintained as close to the patient over the entire range of irradiations. In accordance with the system and methods described herein, preferably an array-shaping collimator such as a multi-leaf collimator, is also positioned with, and upstream of the multi-slit collimator, to define the irradiation field size from each angle.

For whole brain irradiation, the head will be irradiated from all angles, including from underneath the bed. Accordingly, for whole brain irradiation, the bed 66 is preferably made of thin and minimally x-ray absorbing material. Additionally, the bed's head-rest is preferably narrow, i.e., just wide enough to support the head to minimize its interference with the irradiations, and is preferably tapered in the thickness of its lateral edges (see FIG. 2, 104) to allow the multi-slit collimator 80 to slide over it when passing that part of the body during its rotation. Also, referring to FIG. 3, when using positioning elements 96, such as rods, to hold the multi-slit collimator 80 and beam-shaping collimator 90 in its connection in front of the x-ray source 54, a length of the mounting assembly 84, e.g., the distance 89 between the multi-slit collimator 80 and the x-ray source 54, should be adjustable, e.g., using spring-loaded junctions 98 between the positioning elements 96 and the laser source 54, to avoid collision with the bed during rotation of the gantry. In particular embodiments, the irradiation should be administered by rotating the gantry through 360° around the head at the pace that produces the desired dose in the brain.

The system and methods of the present disclosure can also be configured to avoid two problems that may occur in MRT. The first problem could be the excessive gradual broadening of the microbeams as they depart from the multi-slit collimator that produces them. Depending on the microbeams' width and spacing, such broadening can make the microbeams nearly or completely merge with their neighbors in the body of the patient to have their tissue-sparing effect compromised. Such an event can either produce excessive dose of radiation leakage between them, called the "valley dose", or in the extreme case, to produce a solid beam, thus losing the microbeams tissue-sparing effect. The valley dose is produced either by Compton scattering or by the final ranges in tissues of the photo-electrons of Compton electrons set in motion by the microbeam x-rays. Accordingly, embodiments of the system and methods of the present disclosure may be configured such that for a given incident microbeam width, the microbeam broadening is minimized by a) maximizing the distances between the x-ray source 54 and the multi-slit collimator 80, e.g., and b) minimizing the distance between the multi-slit collimator 80 and the patient's skin. Both of these objectives may be best accomplished by using the spring mediated junctions 98 in the positioning elements 96 of the mounting assembly 84, for example (see FIGS. 3 and 4). In this case, the rods with spring mediated junctions 98 and the head support of the patient's head (with tapered edges) is designed in such a way that the length adjustment for the rods 96 is achieved by itself as the gantry rotates around the patient's head, keeping the multi-slit collimator as close as possible to the patient throughout the rotation of the gantry.

The second problem arises from the non-uniformity in the density of microbeams in the tissue produced by the diverging geometry of the CT scanner's beam. While the microbeams in cross-section are parallel and distinct when they irradiate the skin, they are not truly collimated as shown in the example of FIG. 1A, but diverge due to the wide-angle incident CT beam producing the microbeams. Accordingly, the entire brain cannot be irradiated with parallel microbeams at each irradiation angle. Another limitation caused by the incident CT beam's divergence angle, a parallel-beam multi-slit collimator cannot accommodate a diverging incident solid beam.

To solve this problem, in methods of the present disclosure, the irradiations may be carried out in a large number of partial exposures, each using only a few microbeams, widely separated, so that the overlap of adjacent microbeams for each such partial irradiation will be small. This solution not only makes the microbeam irradiations given to the brain from a single multi-slit position more uniform, but also makes the microbeams given from the two opposite directions of the head to coalesce more precisely with each other, without spatial or angular mismatch. It should be noted, however, that assuring that microbeams given from opposite sides of the brain coalesce with each other properly might turn out to be difficult. In that case, the treatment of the whole brain irradiation with microbeams can be implemented by 180° gantry rotation only. Twice higher incident doses may be required for this embodiment.

As an example, the microbeam arrays may be made of 2 to 10 microbeams, and having a thickness in the range of between 0.2 to 0.5 mm thick, with the beam spacing on-center in a range of between 0.6 to 1.2 mm. The in-beam, incident microbeam doses used in this application, in embodiments, may be within a wide range, e.g., 40 to 160 Gy. This range is adequate to ablate certain mitotic cells.

Partial brain irradiation is a special case of the whole brain irradiation described above. This is because, in general, partial brain irradiation with the methods of the disclosure involve the confinement of the exposure to a limited angular range of the gantry rotation and/or over a limited lateral length of the brain exposure.

Different partial brain applications will have their own specific features. As the first example, treating multiple sclerosis (MS) lesions of the brain require higher doses than those envisioned for Alzheimer's disease. In this regard, producing remyelination in the demyelinated MS brain lesions might require higher doses than those indicated in the context of the whole brain microbeam irradiation. It should be noted that in partial brain irradiation, the methods should also incorporate substantially lower beam energies to minimize unnecessary dose to deeper brain.

Applications Involving Microbeam Irradiation of the Spinal Cord

Spinal cord irradiations in accordance with the methods of the present disclosure may be carried out, in embodiments, with the patient's bed 66 aligned with the CT's rotation axis (FIG. 5). However, in contrast to some microbeam irradiations of the brain where it may be desirable to use microbeam arrays parallel to the axis of rotation 52, the planes of the microbeams used in spinal cord irradiation, in certain embodiments, are aligned perpendicular to the axis of rotation 52 of the CT scanner 44.

In embodiments, spinal cord irradiations are performed over a partial volume of the cord. Applications include treating spinal cord injury for functional recovery, and treating spinal cord MS demyelinated lesions to produce remyelination.

In embodiments of the methods of the present disclosure for delivering MRT to a spinal cord, the stationary mode of operation is used. For example, as shown in FIG. 5 and described supra, the x-ray source 54 is rotated at or near its lowest position, i.e., sending the beam vertically—or nearly vertically—upward, with the subject positioned on his/her back lying over the multi-slit collimator 80. For this application, the multi-slit collimator 80 can either be (removably) attached to the inside of the gantry 46, or the multi-slit collimator 80' may be inserted into the bed 66 from one of its sides. The beam-shaping collimator 90 may also be positioned under the bed and held with a positioning system attached to the gantry 46 to keep it in place downstream of the x-ray source 54 and upstream of the multi-slit collimator 80, 80'. Furthermore, as indicated in partial brain irradiation described above, because the dose is intended only for shallow tissue in the spinal cord substantially lower beam energies may be used to minimize unnecessary dose to deeper tissues.

One benefit of the systems and methods of a dual-use system for CT and MRT of the present disclosure is that after the CT imaging, the patient can remain in position for therapy. This provides improved precision of targeting the lesion to be irradiated. Such a targeting precision is significant for such applications as the treatment with microbeams of the spinal cord injury in which the target is defined within a single millimeter precision mostly because the knowledge of the injury site is related to the position of the vertebrae.

Another example of such targeting significance is the treatment of demyelinated MS plaques. Here, although the soft-tissue contrast of the CT images will not be adequate to depict the precise borders of the demyelinated lesion, co-registration of the CT images to MR images taken from the patient in the same position allow the translation of the information regarding the location and the shape of the demyelinated lesion, first from MR image to CT image and then from CT image to microbeam irradiation. Finally, CT images of the brain available with the same location of the patient on the bed allow tailoring of the targeted brain to the area of interest indicated by the CT/MRI. Accordingly, the system and methods of the present dual use CT/MRT allow the use of the multi-leaf collimator for shaping the x-ray beam projected onto the patient to its highest efficiency by producing millimeter-precision targeting.

Features of the system and method of the present disclosure include "on the fly" switching of the scanner's mechanical system to therapy mode without the need for patient re-positioning. The first step in this switching process may be to guide the gantry's mechanical system to switch to the specific configuration used for that particular clinical application. For example, as indicated below, treating spinal cord injury or partial spinal cord irradiation of demyelinated plaques require that the gantry be switched to the stationary mode. In both these cases, the x-ray tube will be located near or at its lowest point, i.e. sending the beam vertically, or nearly vertically, upward towards the subject lying on its' back on the bed with the multi-slit collimator positioned under their spinal cord inside or below the bed.

Embodiments of the system may also include at least two distinct modes of MRT operation, one for brain irradiation and a second one for spinal cord irradiation. For the brain irradiation, the gantry is rotated around the patient's bed and microbeam irradiation is administered either to the entire brain or to a portion of the brain, in embodiments, using arrays of parallel microbeams. For the spinal cord irradiation, both from a single direction and from a limited range of angles, the irradiations are preferably administered from below the bed. For such applications, the bed is preferably made of very thin, minimally x-ray absorbing material.

Components removably mounted with the multi-slit collimator downstream of the x-ray source 54 of the CT scanner, may include, in the order going away from the source, a bow-tie filter, regular beam filter, a beam-sizing and shaping collimator, which may be a multi-leaf collimator, and the multi-slit collimator to produce microbeams or minibeams from incident solid beams. The regular beam filter, and other components which may be mounted together, e.g., via the mounting assembly of the disclosure, may be adjusted as needed to accommodate the specifications of the particular application, and thus are removably mountable and interchangeable depending on the application.

The multi-slit collimator, for example, can is made of a varying number of slits parallel, or nearly parallel, to each other held in a frame. The design of the multi-slit collimator and its positioning depends on the specific clinical application. In general, a consideration for the choice of the dose in each microbeam or minibeam is that it be clinically effective for its specific application without producing a large background, or valley dose, which would act as a solid beam and cause damage to the entire local tissue. This requirement limits not only the dose in each microbeam or minibeam but also limits how close the microbeams could be to each other inside the target tissue. One of skill in the art will appreciate that these considerations are different for whole brain irradiation, partial brain irradiation, and spinal cord irradiation.

The bed 66 of the present disclosure is preferably configured, in embodiments, with additional degrees of freedom not found in CT scanners. For example, in further applications for irradiating targets on the side of the brain, or non-central nervous system (CNS) targets that are not centric to the body, as described supra, the bed preferably includes another degree of freedom, namely for lateral movement 70 (see FIG. 3), besides its two movements of up/down 68 and in/out, i.e., parallel to the rotation axis 52 69. This feature is used in partial brain irradiation when the lesion is not central to the brain. Alternatively, the non-central brain target may be irradiated with microbeams using a large MLC as the array-shaping collimator. In this way the open section of the MLC shifts laterally depending on gantry angle.

Referring again to FIG. 3, for irradiating the entire brain in non-axial planes, the bed includes a fourth degree of freedom, namely for angular rotation 72 about the bed's vertical axis. This may be used to introduce an angular spread among the microbeams' plane of irradiation to minimize interference between consequential exposures. It may also be used for treating the brain in applications where the emphasis is in exposing certain non-centric brain segments.

While the disclosure has been particularly shown and described with reference to specific embodiments, it should be apparent to those skilled in the art that the foregoing is illustrative only and not limiting, having been presented by way of example only. Various changes in form and detail may be made therein without departing from the spirit and scope of the disclosure and equivalents thereof.

What is claimed is:

1. A system for delivering microbeam x-ray radiation therapy to a subject, the system comprising:
    a computed tomography scanner comprising imaging apparatus, a gantry having an inner surface surrounding an opening for positioning a subject therein, an axis of rotation around which the gantry rotates, and an x-ray source mounted to and rotatable with the gantry, the imaging apparatus including detectors positioned on the gantry diametrically opposite the x-ray source and rotatable therewith, and controllers and processors operatively connected to the detectors to collect and process data from the detectors, wherein the computed tomography scanner further includes computer processing hardware and software configured to generate tomographic images, from the data collected from the detectors, of an axial section of a subject positioned within the opening;
    a bed on which the subject is positioned within the opening; and
    a multi-slit collimator removably and operatively mounted to the gantry in front of, and within a trajectory of, the x-ray source for delivering an array of microbeams of therapeutic x-ray radiation to a targeted portion of the axial section identified from the tomographic images, wherein the system is configured to operate in a computed tomography mode for generating the tomographic images using the x-ray source and in a therapeutic x-ray radiation mode using the x-ray source with the multi-slit collimator mounted to the gantry.

2. The system of claim 1, further comprising positioning elements positioned between the x-ray source and the multi-slit collimator to maintain a distance between the x-ray source and the multi-slit collimator, and wherein the positioning elements are operatively connected to the multi-slit collimator, such that the positioning elements and the multi-slit collimator are rotatable with the x-ray source on the gantry.

3. The system of claim 2, wherein the positioning elements include rods configured to fix the distance between the multi-slit collimator and the x-ray source.

4. The system of claim 2, further including a mounting assembly comprising the multi-slit collimator and the positioning elements, wherein the mounting assembly is configured to be removably and operatively mounted to the gantry such that the multi-slit collimator is within the trajectory of the x-ray source, and wherein the positioning elements comprise spring-loaded junctions operatively connecting the x-ray source to the multi-slit collimator, a distance between the multi-slit collimator and the x-ray source being springedly shortened upon contact of a distal end of the mounting assembly with the bed.

5. The system of claim 4, the mounting assembly further comprising a beam-shaping collimator positioned upstream of the multi-slit collimator, the beam-shaping collimator being positioned on the mounting assembly between the multi-slit collimator and the positioning elements.

6. The system of claim 5, wherein the beam-shaping collimator is a multi-leaf collimator.

7. The system of claim 5, wherein the multi-slit collimator is aligned to generate the microbeams in planes perpendicular to the axis of rotation, and wherein the system further includes a control module including processors, in communication with controllers and motors that operate the gantry and the beam-shaping collimator, wherein the processors are configured to implement executable steps to operate the system to deliver the array of microbeams continuously over a predetermined angle of rotation of the gantry and to continuously adjust the beam-shaping collimator to correspond to a shape of the targeted portion in a trajectory of the x-ray source over the predetermined angle of rotation.

8. The system of claim 5, wherein the multi-slit collimator is aligned to generate the microbeams in planes parallel to the axis of rotation, and wherein the system further includes a control module including processors, in communication with the x-ray source and with controllers and motors that operate the gantry and the beam-shaping collimator, wherein the processors are configured to implement executable steps to operate the system to deliver the array of microbeams in step-wise adjacent irradiation exposures over a rotation of the gantry over a predetermined range of angles, and to adjust the beam-shaping collimator to correspond to a shape of the targeted portion in a trajectory of the x-ray source at each step-wise adjacent irradiation.

9. The system of claim 1, wherein a position of the bed is adjustable horizontally along the axis of rotation and laterally thereto, and is also adjustable up and down along a vertical axis, and angularly around the vertical axis.

10. The system of claim 1, wherein the microbeam radiation therapy mode of the system includes a stationary mode of operation, wherein the gantry is rotated to and then fixed at a position to irradiate the targeted portion, wherein the gantry is stationary at the position during irradiation of the targeted portion.

11. The system of claim 1, wherein the bed includes a headrest having a width defined along a lateral direction to the rotation of axis of the gantry that is narrower than a body-resting portion of the bed, and wherein the bed is further tapered in thickness at its lateral edges.

12. The system of claim 1, wherein each of the microbeams in the array has a thickness in a range of between 20 microns to 1 millimeter, and a center-to-center spacing in a range of between 2 to 10 times the thickness.

13. The system of claim 1, wherein the x-ray source is a rotating anode source operating in a range of between 70 kVp to 150 kVp and having a spot size between 0.2 mm to 1.0 mm.

14. A system for delivering microbeam x-ray radiation therapy to a subject, the system comprising:
a computed tomography scanner comprising imaging apparatus, a gantry having an inner surface surrounding an opening for positioning a subject therein, an axis of rotation around which the gantry rotates, and an x-ray source mounted to and rotatable with the gantry, the imaging apparatus including detectors positioned on the gantry diametrically opposite the x-ray source and rotatable therewith, and controllers and processors operatively connected to the detectors to collect and process data from the detectors, wherein the computed tomography scanner further includes computer processing hardware and software configured to generate tomographic images, from the data collected from the detectors, of an axial section of a subject positioned within the opening;
a bed on which the subject is positioned within the opening;
a multi-slit collimator operatively mounted to the gantry in front of, and within a trajectory of, the x-ray source for delivering an array of microbeams of therapeutic x-ray radiation to a targeted portion of the axial section;
a shutter formed of an x-ray absorbing material, wherein the shutter is configured to cover and protect the detectors from the array of therapeutic x-ray radiation; and
a control module configured to operate in a computed tomography scanner mode, and to switch to, and operate in, a microbeam radiation therapy mode to deliver microbeam radiation therapy to the subject with the multi-slit collimator positioned within the trajectory of the x-ray source, and wherein the shutter is operable to automatically cover the detectors in the microbeam radiation therapy mode.

15. The system of claim 14, the system further comprising a sensor monitoring an operational parameter of the x-ray source in the microbeam radiation therapy mode, and a safety switch operatively connected to the x-ray source and in communication with the sensor, the safety switch configured to automatically shut down the x-ray source in response to the operational parameter exceeding a pre-determined threshold.

16. The system of claim 15, wherein the operational parameter is one of an operating temperature of the x-ray source and a time of continuous operation of the x-ray source.

17. A system for delivering microbeam x-ray radiation therapy to a subject, the system comprising:
a computed tomography scanner comprising imaging apparatus, a gantry having an inner surface surrounding an opening for positioning a subject therein, an axis of rotation around which the gantry rotates, and an x-ray source mounted to and rotatable with the gantry, the imaging apparatus including detectors positioned on the gantry diametrically opposite the x-ray source and rotatable therewith, and controllers and processors operatively connected to the detectors to collect and process data from the detectors, wherein the computed tomography scanner further includes computer processing hardware and software configured to generate tomographic images, from the data collected from the detectors, of an axial section of a subject positioned within the opening;
a bed on which the subject is positioned within the opening; and
a multi-slit collimator for delivering an array of microbeams of therapeutic x-ray radiation to a targeted portion of the axial section, wherein the targeted portion corresponds to a portion of a spinal cord, and wherein the multi-slit collimator is mounted to the bed at a position along a central axis of the bed corresponding to the targeted portion, and wherein the x-ray source is rotatable with the gantry to a location underneath the bed, and wherein the bed, with the multi-slit collimator mounted at the position thereto, is adjustably positioned such that the multi-slit collimator is positioned within the trajectory of the x-ray source to irradiate the targeted portion of the spinal cord with the microbeams vertically upward from beneath the bed.

* * * * *